(12) United States Patent
Chung et al.

(10) Patent No.: US 8,394,512 B2
(45) Date of Patent: Mar. 12, 2013

(54) PHOSPHAPHENANTHRENE COMPOUNDS AND ORGANIC LIGHT EMITTING DIODE USING THE SAME

(75) Inventors: Kwang Choon Chung, Gyeonggi-do (KR); Hyun-Nam Cho, Gyeonggi-do (KR); Ik-Kyu Park, Gyeonggi-do (KR); Ji-Hoon Yoo, Gyeonggi-do (KR); Ae-Ran Hyun, Seoul (KR); Yun-Ho Jung, Gyeonggi-do (KR)

(73) Assignee: Inktec Co., Ltd. (KR)

( * ) Notice: Subject to any disclaimer, the term of this patent is extended or adjusted under 35 U.S.C. 154(b) by 404 days.

(21) Appl. No.: 12/594,716

(22) PCT Filed: Apr. 5, 2008

(86) PCT No.: PCT/KR2008/001943
§ 371 (c)(1),
(2), (4) Date: May 14, 2010

(87) PCT Pub. No.: WO2008/123722
PCT Pub. Date: Oct. 16, 2008

(65) Prior Publication Data
US 2010/0252818 A1    Oct. 7, 2010

(30) Foreign Application Priority Data

Apr. 5, 2007   (KR) ........................ 10-2007-0033521
Apr. 4, 2008   (KR) ........................ 10-2008-0031843

(51) Int. Cl.
*H01L 51/54*     (2006.01)

(52) U.S. Cl. ........ 428/690; 428/917; 313/504; 313/505; 313/506; 257/40; 257/E51.05; 257/E51.026; 257/E51.032; 558/73; 558/82

(58) Field of Classification Search .................... 558/73, 558/82, 398; 428/690, 917; 313/504, 505; 257/40, E51.05, E51.026, E51.032
See application file for complete search history.

(56) References Cited

U.S. PATENT DOCUMENTS
2005/0239975 A1   10/2005   Gan et al.

FOREIGN PATENT DOCUMENTS

| | | | |
|---|---|---|---|
| EP | 1243641 A1 | | 9/2002 |
| EP | 1512690 A1 | | 3/2005 |
| JP | 61118392 | | 6/1986 |
| JP | 63185992 | | 8/1988 |
| JP | 2000191953 | | 7/2000 |
| JP | 2000239491 | | 9/2000 |
| JP | 2001064356 | | 3/2001 |
| JP | 2005053857 | | 3/2002 |
| JP | 2004292495 | | 10/2004 |
| JP | 2005179439 | | 7/2005 |
| JP | 2006-063243 | * | 3/2006 |
| JP | 2006063243 | | 3/2006 |
| JP | 2006063258 | | 3/2006 |
| JP | 2006328100 | | 12/2006 |
| JP | 2007-146131 | * | 6/2007 |
| WO | 03102060 | | 12/2003 |
| WO | 03102060 A1 | | 12/2003 |
| WO | 2006027241 | | 3/2006 |
| WO | 2006027241 A1 | | 3/2006 |

OTHER PUBLICATIONS

Chinese Office Action—Chinese Application No. 200880014887.2 issued on Jun. 4, 2012, citing CN1659217 and "Synthesis and luminescent characteristics of novel phosphorus containing light-emitting polymers".
Y. M. Sun, et al., Synthesis and luminescent characteristics of novel phosphorus containing light-emitting polymers, Polymer, vol. 42, p. 1035-1045.
Sun et al. "Synthesis and luminescent characteristics of novel phosphorus containing light-emitting polymers" Polymer 42, 2001, pp. 1035-1045.
European Search Report for application No. 08741193.0-1218/ 2134808 dated Jun. 15, 2011.
Y. M. Sun, et al., Synthesis and luminescent characteristics of novel phosphorus containing light-emitting polymers, Polymer 42, 2001, p. 1035-1045.
G. Lligadas, et al., Synthesis and Properties of Thermosetting Polymers from a Phosphorous-Containing Fatty Acid Derivative, Journal of Polymer Science, vol. 44, p. 5630-5644.
I. P. Beletskaya, et al., Arylation of 6H-Dibenzo-oxaphosphinine 6-Oxide, Russian Journal of Organic Chemistry, vol. 40, No. 12, 2004, p. 1782-1786.
G. Keglevich, et al., 2-Aryl-dibenzo-1,2-oxaphosphotine as a Ligand in Borane and in Pt(II) Complexes, Heteroatom Chemistry, vol. 15, No. 6, 2004, p. 459-463.

* cited by examiner

*Primary Examiner* — Jennifer A Chriss
*Assistant Examiner* — Gregory Clark
(74) *Attorney, Agent, or Firm* — Cantor Colburn LLP

(57) ABSTRACT

The present invention relates to new phosphaphenanthrene compounds with excellent light emitting property and an organic light emitting diode (OLED) using the same.

15 Claims, 7 Drawing Sheets

PHOSPHAPHENANTHRENE COMPOUNDS AND ORGANIC LIGHT EMITTING DIODE USING THE SAME

TECHNICAL FIELD

The present invention relates to phosphaphenanthrene compounds being phosphorous compounds with light emitting property and an organic light emitting diode (hereinafter, referred to as OLED) with excellent light emitting property using the same.

BACKGROUND ART

An OLED, which is a self-light emitting display, has several advantages of wide viewing angle, rapid response speed, low voltage driving, etc. and has currently been used as a next-generation flat panel display.

A general OLED is basically configured of a multi-layer thin film structure made of organic compounds, such as a hole transporting layer, a light emitting layer, an electron transporting layer, and a hole transporting layer between a cathode and an anode of the OLED, etc. The OLED uses a principle that when electricity is applied between both electrodes, recombines electrons with holes at the light emitting layer by the injection of electrons from the cathode and the injection of holes from the anode and emits light during the drop of energy level from an excited state to a ground state.

Since it has been announced that the OLED using aromatic diamine and Alq3 as materials for forming the light emitting layer is first developed by Eastman Kodak Co. (USA) on 1987 (Appl. Phys. Lett. p 913, (1987)), a study intending to improve performance of naphthyldiamine-based light emitting materials (U.S. Pat. No. 6,549,345), fluorescent-type light emitting materials (U.S. Pat. No. 6,803,121) such as anthracene-based materials, and phosphor-type light emitting materials such as light emitting materials using iridium complex with more excellent efficiency (U.S. Pat. No. 6,858,327) has been progressed. Today, the OLED has actually been applied to a small flat panel display, such as a mobile phone, etc.

As blue light emitting compounds known up to now, there are distryl-based anthrancene derivatives developed by Idemitsu Kosan (EP 388, 768 (1990), Kyushu University (PRO, SRIE, 1910, 180(1993)), or the like. However, the blue light emitting materials have light emitting efficiency lower than light emitting bodies of other colors and should further be improved in thin film stability, heat resistance, etc.

Meanwhile, it is common to use host materials as the phosphor-type light emitting materials so as to maximize efficiency through energy transfer. For example, as low molecular phosphor hosts, there are 4,4'-N,N'-dicarbazole-biphenyl (CBP), 1,3-bis(9-carbazolyl)benzene (mCP), etc (Journal of Materials chemistry (2003) 13, 2157-2163; Journal of Materials chemistry (2005) 15, 2304-2315), as polymeric phosphor hosts, there are poly(N-vinylcarbazole) (PVK), etc. Recently, C. W. Tang group reported that an organic light emitting diode with a single layer structure and a multi-layer structure uses the polymeric polyvinylcarbazole as the phosphor host, instead of using the CBP and the mCP as the phosphor hosts (J. Appl. Phys., Vol. 92, No. 7, 3447). However, the organic light emitting diode has a disadvantage of deterioration of devices by driving heat generated when it is driven for a long time. In particular, since the material, such as the mCP, has low glass transition temp. −Tg, it is easily crystallized into the thin film material when the device is driven, thereby causing a large disadvantage of a change in color purity and a reduction in device lifetime by the driving heat. Therefore, in material development for the long-time and high-efficiency OLED, the heat resistance as an important variable in addition to the color purity and the efficiency has been considered as an important variable.

The inventors have developed materials with excellent light emitting property as well as heat resistance by introducing phosphaphenanthrene derivatives being phosphorous compounds as materials for the OLED from their continued efforts and have successfully performed the OLED configuration using the same.

The phosphaphenanthrene derivatives have been used as only flame retardant, etc. (KR patent publication 1993-3867), but have little example used as materials for the OLED. Polymer materials including phosphaphenanthrene compounds used as the materials for the OLED is known in US Laid-Open No. 2002-0193522 of the related art. As the phosphaphenanthrene compounds included in the polymer materials, the following three compounds are known. However, the known technology is limited to the following three compounds and is not applied to EL.

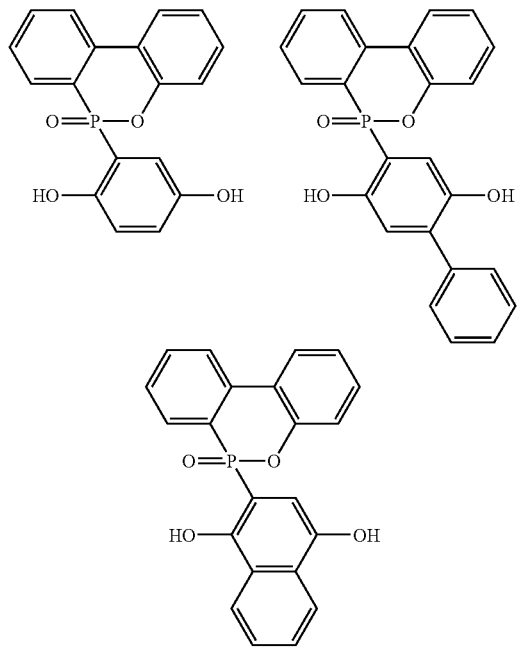

DISCLOSURE

Technical Problem

An object of the present invention provides phosphaphenanthrene compounds with heat resistance and excellent light emitting property required for implementing a high-efficiency and long-lifetime device as described above. Another object of the present invention provides an organic light emitting diode containing prepared phosphaphenanthrene compounds as light-emitting materials.

Technical Solution

The present invention relates to phosphaphenanthrene compounds with excellent heat resistance and light emitting property represented by the following chemical formula 1 usable as core materials for an OLED and an organic light emitting diode including the same as light emitting materials.

[Chemical Formula 1]

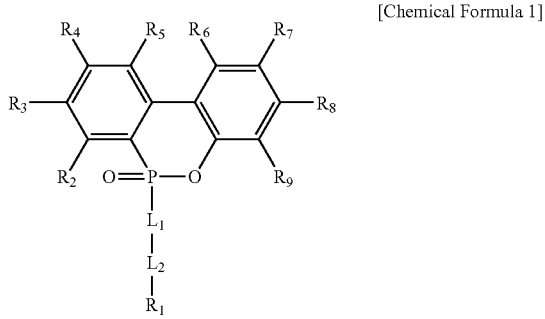

[In the chemical formula 1, $L_1$ is chemical bond or $(C_2-C_{10})$ alkenylene, $(C_6-C_{30})$ arylene or $NR_{11}$, and alkenylene or arylene of the $L_1$ may further be substituted into at least one selected from $(C_1-C_{22})$ alkyl, $(C_6-C_{30})$ aryl, $(C_2-C_{30})$ heteroaryl, $(C_6-C_{30})$ ar $(C_1-C_{22})$ alkyl, $(C_1-C_{22})$ alkyl $(C_6-C_{30})$ aryl, halogen, $(C_1-C_{10})$ alkylsilyl, $(C_6-C_{30})$arylsilyl, carboxylic acid, cyano, or $OR_{31}$;

$L_2$ is $(C_2-C_{10})$ alkenylene, $(C_2-C_{10})$ alkynylene, $(C_6-C_{30})$ arylene, $(C_2-C_{30})$ heteroarylene or —$Ar_1$-A-$Ar_2$—, and alkenylene, arylene, or heteroarylene of the $L_2$ may further be substituted into at least one selected from $(C_1-C_{22})$ alkyl, halogen, cyano, carboxylic acid, $(C_1-C_{10})$ alkylsilyl, $(C_6-C_{30})$ arylsilyl, $(C_6-C_{30})$ aryl, $(C_2-C_{30})$ heteroaryl, $(C_6-C_{30})$ar $(C_1-C_{22})$alkyl, $(C_1-C_{22})$ alkyl $(C_6-C_{30})$ aryl or $OR_{31}$;

$Ar_1$ and $Ar_2$ are independent from each other and are $(C_6-C_{30})$ arylene or $(C_2-C_{30})$ heteroarylene, and arylene or heteroarylene of the $Ar_1$ and $Ar_2$ may further be substituted into at least one selected from $(C_1-C_{22})$alkyl, $(C_6-C_{30})$aryl, $(C_6-C_{30})$aryloxy, $(C_2-C_{30})$heteroaryl, halogen, $(C_1-C_{10})$alkylsilyl, $(C_6-C_{30})$arylsilyl, $(C_1-C_{22})$alkoxy, carboxylic acid or cyano;

A is $NR_{12}$, $(O=)PR_{13}$, $SiR_{14}R_{15}$, $SO_2$ or O;

$R_1$ is hydrogen, $(C_1-C_{22})$alkyl, $(C_6-C_{30})$aryl, $(C_2-C_{30})$heteroaryl, halogen, cyano, $(C_1-C_{22})$alkoxy, $(C_6-C_{30})$aryloxy, $(C_6-C_{30})$arylsulfonyl, mono- or di$(C_1-C_{10})$alkylamino, mono- or di$(C_6-C_{30})$arylamino, $(C_2-C_7)$alkenyloxy, $(C_2-C_7)$alkynyloxy, $(C_2-C_7)$alkenylcarbonyloxy, $(C_2-C_7)$alkynylcarbonyloxy, $(C_1-C_{10})$alkylsilyl, $(C_6-C_{30})$arylsilyl or

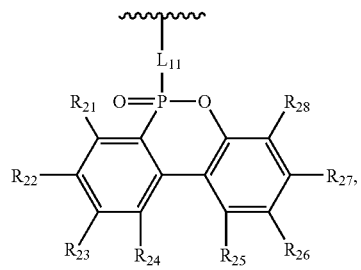

and alkyl, aryl, heteroaryl, alkoxy, aryloxy, arylsulfonyl, alkylamino, arylamino, alkenyloxy, alkynyloxy, alkylsilyl or arylsilyl of the $R_1$ may further be substituted into at least one selected from $(C_1-C_{10})$alkyl, halogen, cyano, nitro, carboxylic acid, $(C_6-C_{30})$aryl, mono- or di$(C_1-C_{10})$alkylamino, mono- or di$(C_6-C_{30})$arylamino, $(C_1-C_{10})$alkylsilyl, or $(C_6-C_{30})$arylsilyl;

$L_{11}$ is chemical bond or $(C_2-C_{10})$alkenylene, $(C_6-C_{30})$arylene or $NR_{16}$, and alkenylene or arylene of the $L_{11}$ may further be substituted into at least one selected from $(C_1-C_{22})$ alkyl, $(C_1-C_{22})$alkoxy, $(C_3-C_{22})$ cycloalkyl, $(C_6-C_{30})$aryl, cyano, halogen, amino, mono- or di$(C_1-C_{10})$alkylamino, mono- or di$(C_6-C_{30})$arylamino, nitro, or hydroxy;

$R_2$ to $R_9$ are independent from each other and are hydrogen, $(C_1-C_{22})$alkyl, $(C_1-C_{22})$alkyl including oxygen, nitrogen, or sulfur, $(C_1-C_{22})$alkoxy, $(C_3-C_{22})$ cycloalkyl, $(C_3-C_{22})$ cycloalkyl $(C_1-C_{22})$alkyl, $(C_6-C_{30})$aryl, halogen, cyano, amino, mono- or di$(C_1-C_{10})$alkylamino, mono- or di$(C_6-C_{30})$ arylamino, hydroxy, nitro, mono- or di-benzylamino, or $(C_3-C_{10})$cycloalkylamino and the $R_2$ to $R_9$ are combined with carbon of neighboring substitutent by $(C_3-C_5)$alkylene or $(C_3-C_5)$alkenylene to form a fused ring, carbon of the fused ring may be substituted into heteroatoms selected from oxygen, sulfur, or nitrogen, and alkyl, alkoxy, cycloalkyl, cycloalkylalkyl, aryl, or amino of the $R_2$ to $R_9$ may further be substituted into at least one selected from $(C_1-C_{10})$alkyl, halogen, $(C_6-C_{30})$aryl, $(C_1-C_{10})$alkylsilyl, or $(C_6-C_{30})$arylsilyl;

$R_{11}$ to $R_{16}$ are independent from each other and are $(C_1-C_{22})$alkyl, $(C_3-C_{22})$ cycloalkyl, $(C_6-C_{30})$aryl, mono- or di$(C_1-C_{10})$alkylamino, mono- or di$(C_6-C_{30})$arylamino, or amino, and alkyl, cycloalkyl, or aryl of the $R_{11}$ to $R_{16}$ may further be substituted into at least one selected from halogen, $(C_1-C_{22})$alkyl, $(C_6-C_{30})$aryl, $(C_1-C_{22})$alkoxy, 3-member to 7-member heterocycloalkyl including at least one of oxygen, nitrogen, or sulfur, or cyano;

$R_{21}$ to $R_{28}$ are independent from each other and are hydrogen, $(C_1-C_{22})$alkyl, $(C_1-C_{22})$alkyl including oxygen, nitrogen, or $(C_3-C_{22})$cycloalkyl, $(C_3-C_{22})$cycloalkyl $(C_1-C_{22})$ alkyl, $(C_6-C_{30})$aryl, halogen, cyano, amino, mono- or di$(C_1-C_{10})$alkylamino, mono- or di$(C_6-C_{30})$arylamino, hydroxy, nitro, mono- or di-benzylamino, or $(C_3-C_{10})$cycloalkylamino and the $R_{21}$ to $R_{28}$ are combined with carbon of neighboring substitutent by $(C_3-C_5)$alkylene or $(C_3-C_5)$alkenylene to form a fused ring, carbon of the fused ring may be substituted into heteroatoms selected from oxygen, sulfur, or nitrogen, and alkyl, alkoxy, cycloalkyl, cycloalkylalkyl, aryl, or amino of the $R_{21}$ to $R_{28}$ may further be substituted into at least one selected from $(C_1-C_{10})$alkyl, halogen, $(C_6-C_{30})$aryl, $(C_1-C_{10})$ alkylsilyl, or $(C_6-C_{30})$arylsilyl; and $R_{31}$ is $(C_1-C_{22})$alkyl, $(C_6-C_{30})$aryl, $(C_2-C_{10})$alkenyl, or $(C_1-C_{22})$alkylcarbonyl and alkyl, aryl, or alkycarbonyl of the $R_{31}$ may further be substituted into at least one selected from 3-member to 5-member heterocycloalkyl including at least one from N, O, and S, $(C_3-C_{22})$cycloalkyl, $(C_2-C_{10})$alkynyl, $(C_2-C_{10})$alkenyl, cyano, or halogen.]

The $(C_6-C_{30})$aryl group is preferably $(C_6-C_{18})$aryl group and more preferably $(C_6-C_{12})$aryl group. A concrete example of the aryl group may include an aromatic group, such as phenyl, naphthyl, biphenyl, tetrahydronaphthyl, indanyl, fluorenyl, phenanthreneyl, anthracenyl, triphenylenyl, pyrenyl, crycenyl, naphtacenyl.

The $(C_2-C_{30})$ heteroaryl group is preferably $(C_3-C_{18})$ heteroaryl group and more preferably $(C_3-C_{12})$ heteroaryl group. The heteroaryl group may include 1 to 3 heteroatoms selected among N, O, P, or S as aromatic ring structure atoms, wherein the other aromatic ring structure atoms mean an aryl group being carbon. The hetero aryl group includes, for example, a divalent aryl group forming N-oxide or quaternary salt by oxidizing or quartering heteroatoms in the ring. A representative example may include furyl, pyranyl, isobenzofuranyl, pyrrolyl, imidazolyl, pyrazolyl, isothiazolyl, isoxazolyl, tetrazolyl, pyridyl, pyrazinyl, pyrimidinyl, pyridazinyl, indolizinyl, isoindolyl, indolyl, indazolyl, quinolizinyl, isoquinolyl, quinolyl, carbazolyl, phenanthridinyl and N-oxide (for example, pyridyl N-oxide, quinolyl N-oxide) corresponding thereto, and quaternary salt thereof, or the like, but is not limited thereto.

In the phosphaphenanthrene compounds of the chemical formula 1 according to the present invention,

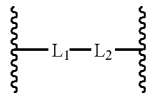

Is selected from the following structure, but is not limited thereto.

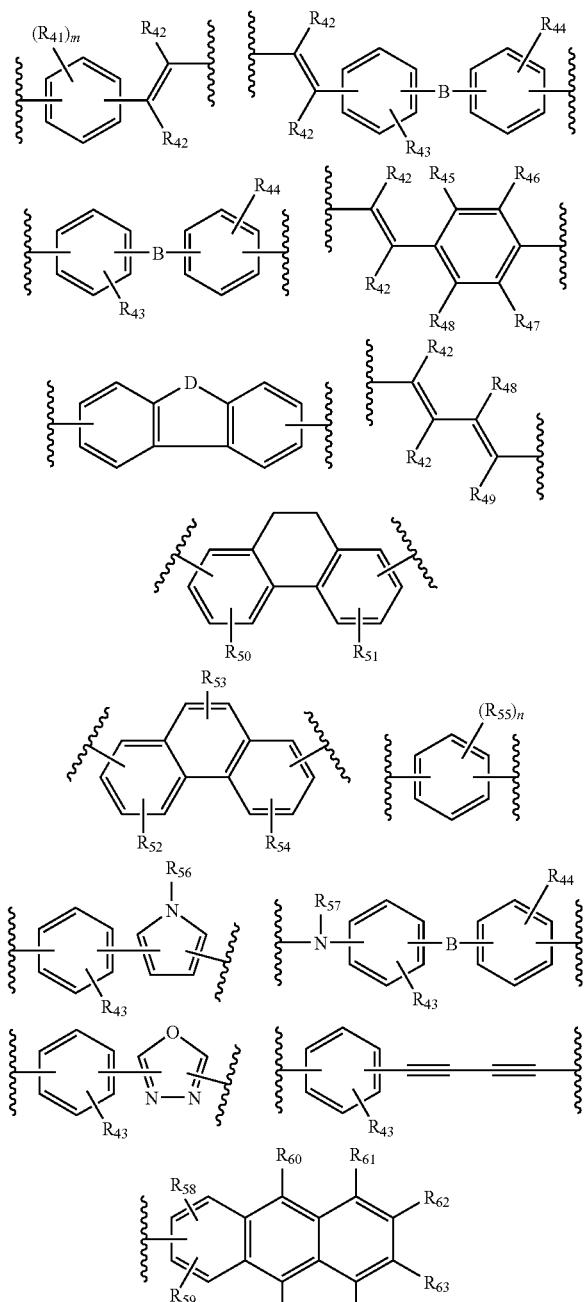

[B is chemical bond or $NR_{71}$, $(O=)PR_{71}$, $SiR_{73}R_{74}$, $SO_2$, or O;

D is $CR_{81}R_{82}$, $NR_{83}$, O, S, or $SO_2$;

$R_{31}$ is $(C_1\text{-}C_{22})$alkyl, $(C_6\text{-}C_{30})$aryl, $(C_2\text{-}C_{10})$alkenyl, or $(C_1\text{-}C_{22})$alkylcarbonyl, and alkyl, alkenyl, or alkycarbonyl of the $R_{31}$ may further be substituted into at least one selected from 3-member to 5-member heterocycloalkyl including at least one from N, O, and S, $(C_3\text{-}C_{22})$cycloalkyl, $(C_2\text{-}C_{10})$alkynyl, $(C_2\text{-}C_{10})$alkenyl, cyano, or halogen;

$R_{41}$ to $R_{64}$ are independent from each other and are hydrogen, $(C_1\text{-}C_{22})$alkyl, $(C_6\text{-}C_{30})$aryl, halogen, $(C_2\text{-}C_{30})$heteroaryl, cyano, carboxylic acid, $(C_1\text{-}C_{10})$alkylsilyl, $(C_6\text{-}C_{30})$arylsilyl, $(C_6\text{-}C_{30})$ ar$(C_1\text{-}C_{22})$alkyl, $(C_1\text{-}C_{22})$alkyl $(C_6\text{-}C_{30})$aryl or $OR_{31}$, or $R_{45}$ and $R_{46}$ or $R_{47}$ and $R_{48}$ are coupled with $(C_3\text{-}C_5)$alkylene or $(C_3\text{-}C_6)$alkenylene to form a fused ring, and carbon of the fused ring may be substituted into heteroatoms selected from oxygen, sulfur, or nitrogen;

$R_{71}$ to $R_{74}$ are independent from each and are $(C_1\text{-}C_{22})$alkyl, $(C_3\text{-}C_{22})$cycloalkyl, $(C_6\text{-}C_{30})$aryl, mono- or di$(C_1\text{-}C_{10})$alkylamino, mono- or di$(C_6\text{-}C_{30})$arylamino, or amino, and alkyl, cycloalkyl, or aryl of the $R_{71}$ to $R_{74}$ may further be substituted into at least one selected from halogen, $(C_1\text{-}C_{22})$alkyl, $(C_6\text{-}C_{30})$aryl, $(C_1\text{-}C_{22})$alkoxy, 3-member to 7-member heterocycloalkyl including at least one of oxygen, nitrogen, or sulfur, or cyano;

$R_{81}$ to $R_{83}$ are independent from each other and are hydrogen, $(C_1\text{-}C_{22})$alkyl, $(C_6\text{-}C_{30})$aryl, halogen, $(C_2\text{-}C_{30})$heteroaryl, cyano, carboxylic acid, $(C_1\text{-}C_{10})$alkylsilyl, $(C_6\text{-}C_{30})$arylsilyl, $(C_6\text{-}C_{30})$ar$(C_1\text{-}C_{22})$alkyl, $(C_1\text{-}C_{22})$alkyl $(C_6\text{-}C_{30})$aryl, or $(C_1\text{-}C_{22})$alkoxy; and m and n are independent from each other and are integers of 1 to 4.]

Specifically, the

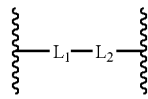

is selected from the following chemical structure.

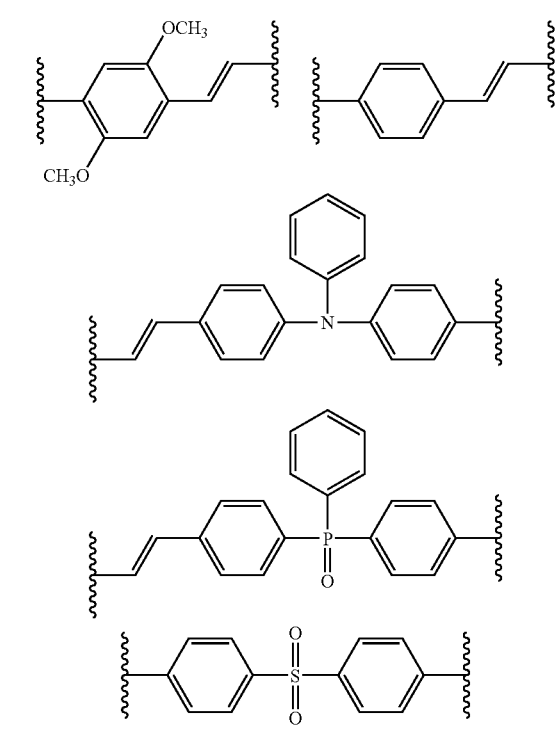

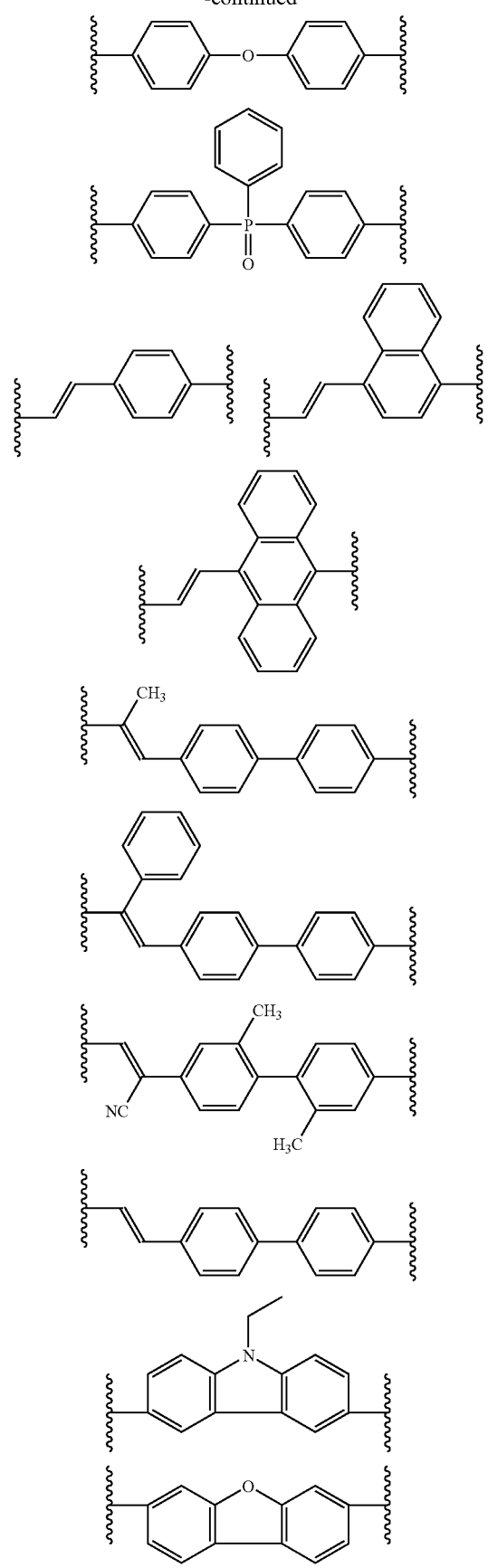
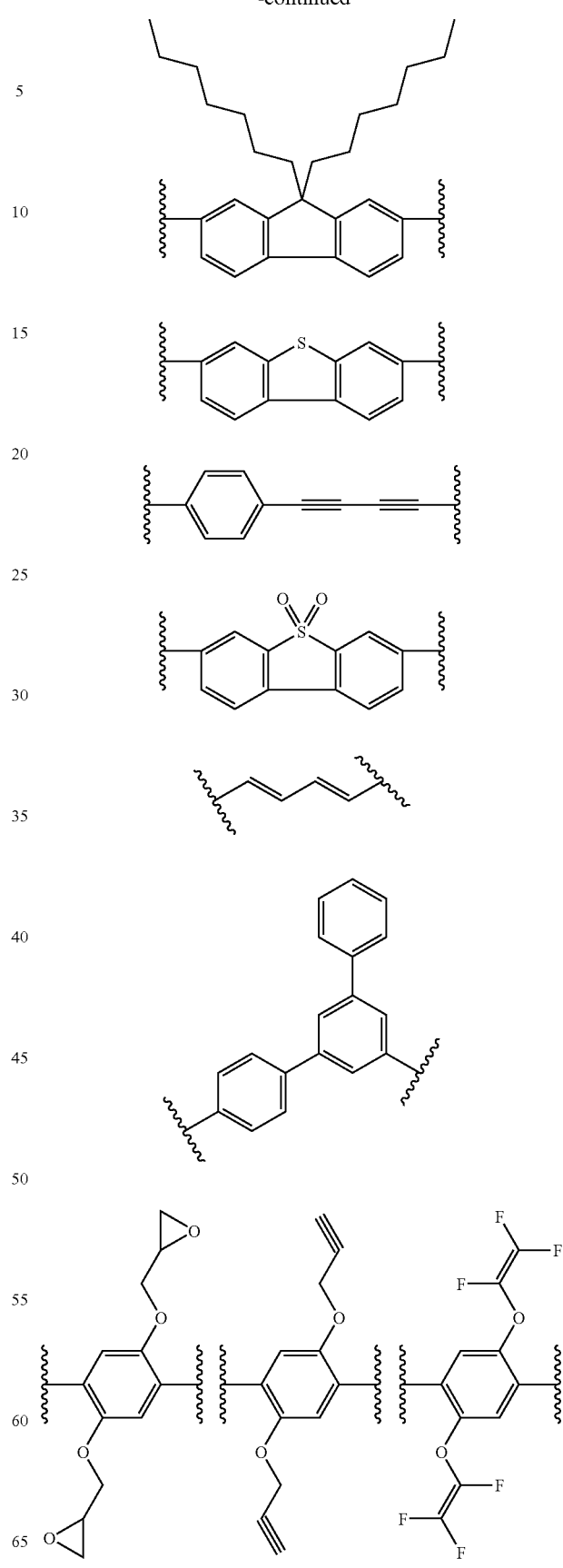

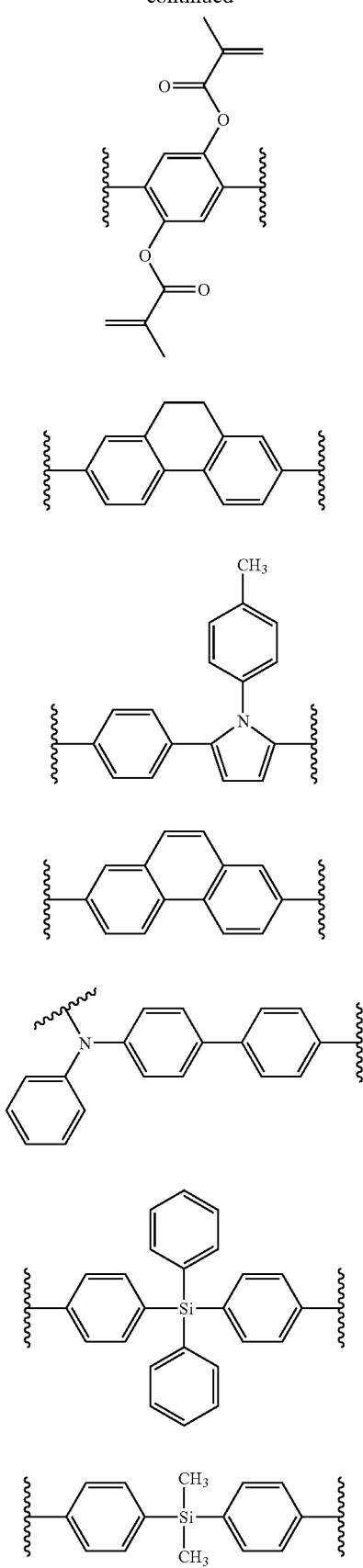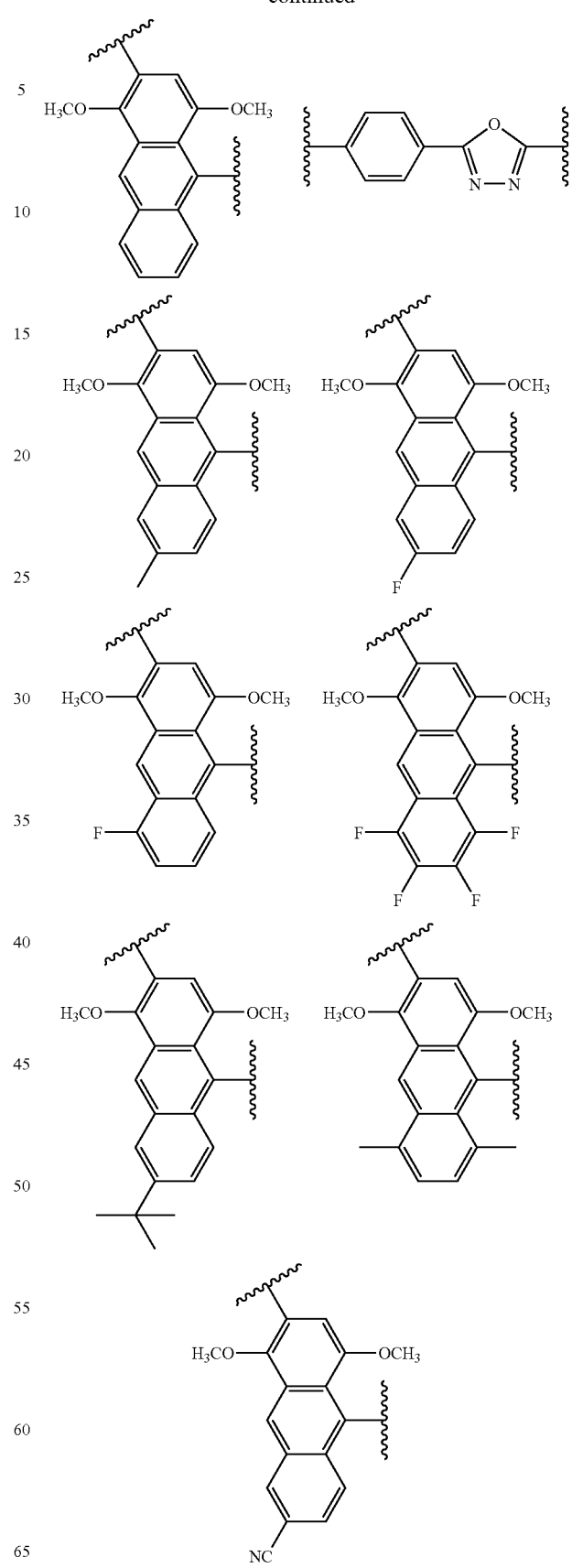

-continued
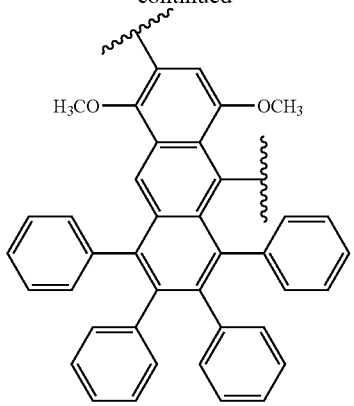
The phosphaphenanthrene compounds according to the present invention may be illustrated by the following compounds, but the present invention is not limited to the following compounds.
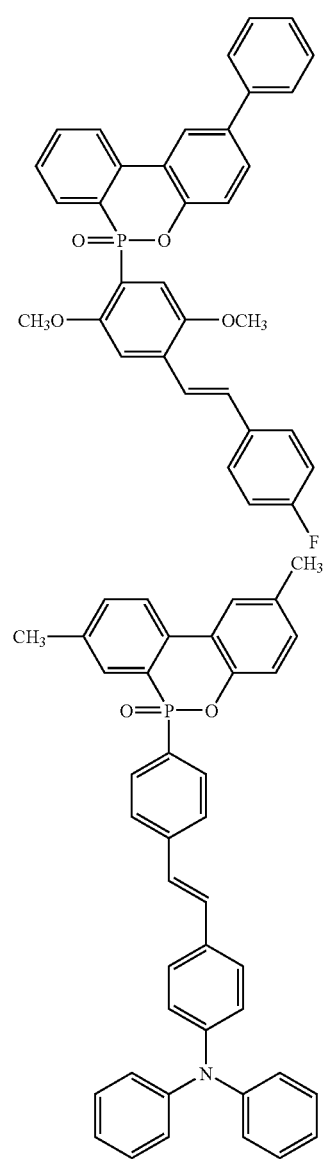
-continued
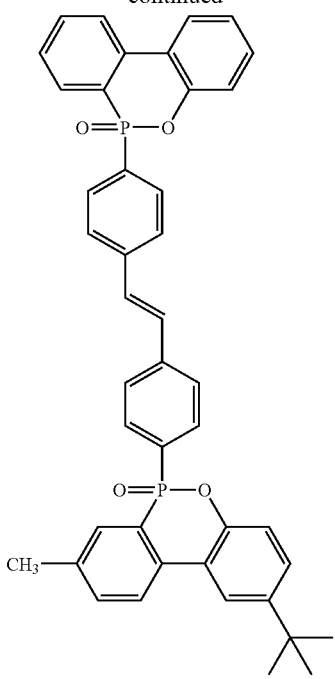
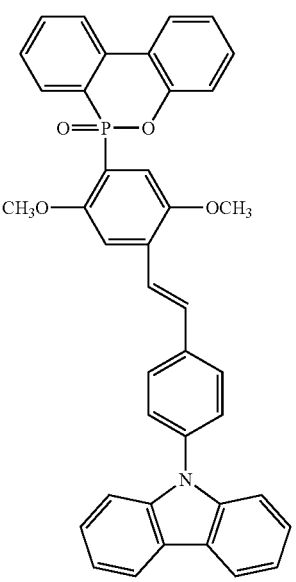

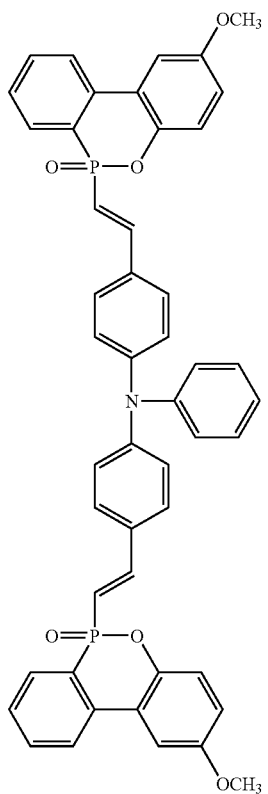
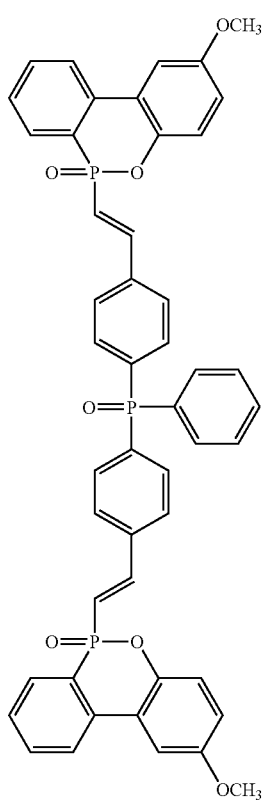
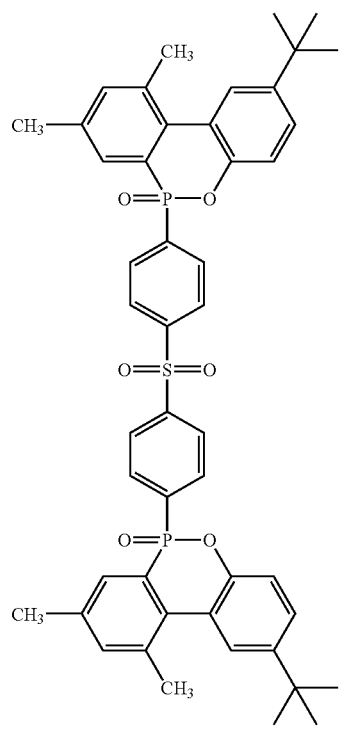
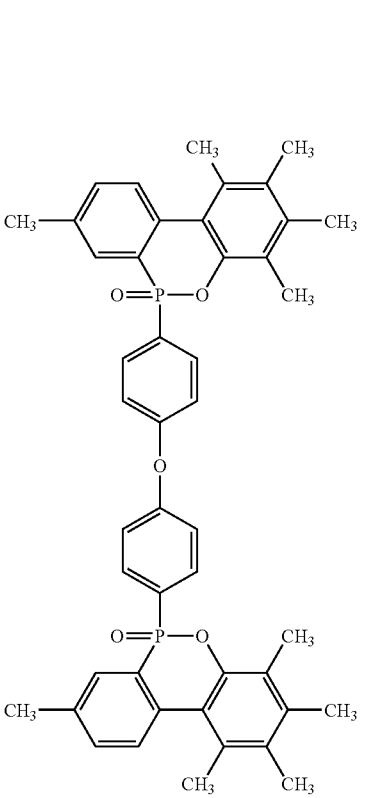

15
-continued
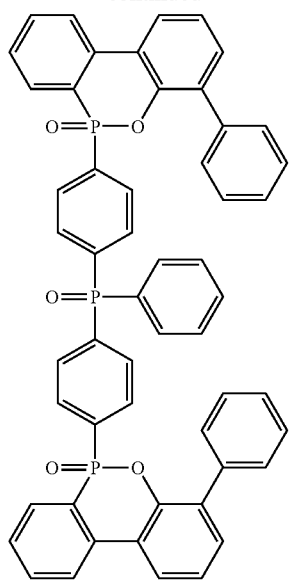
16
-continued
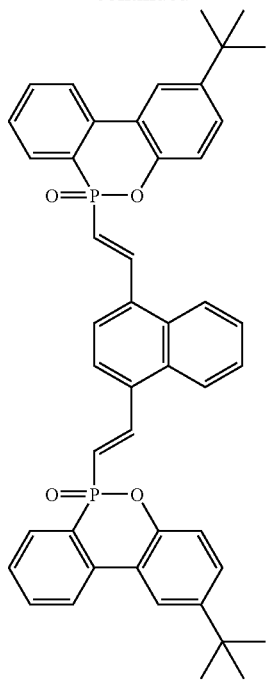
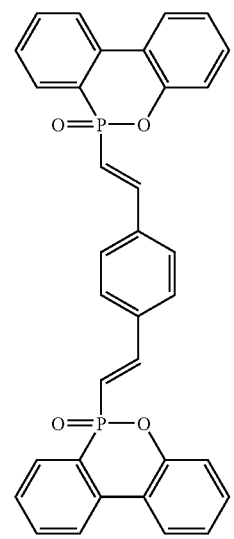
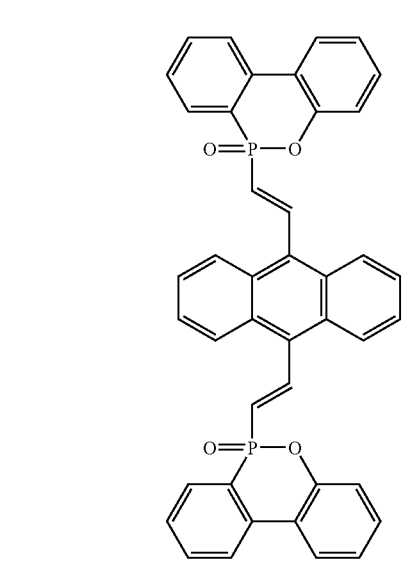

17
-continued
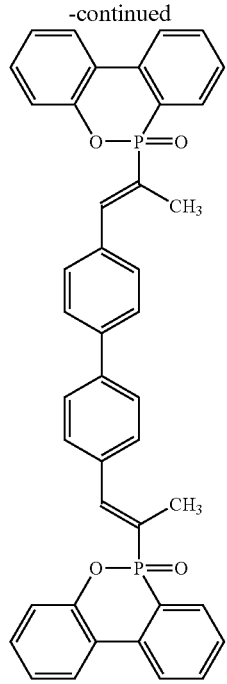
18
-continued
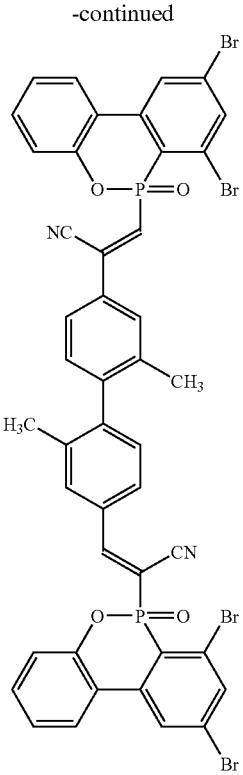
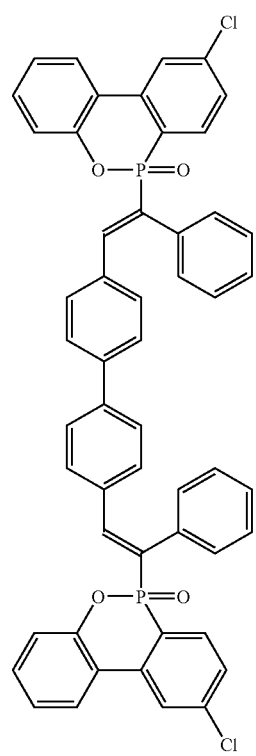

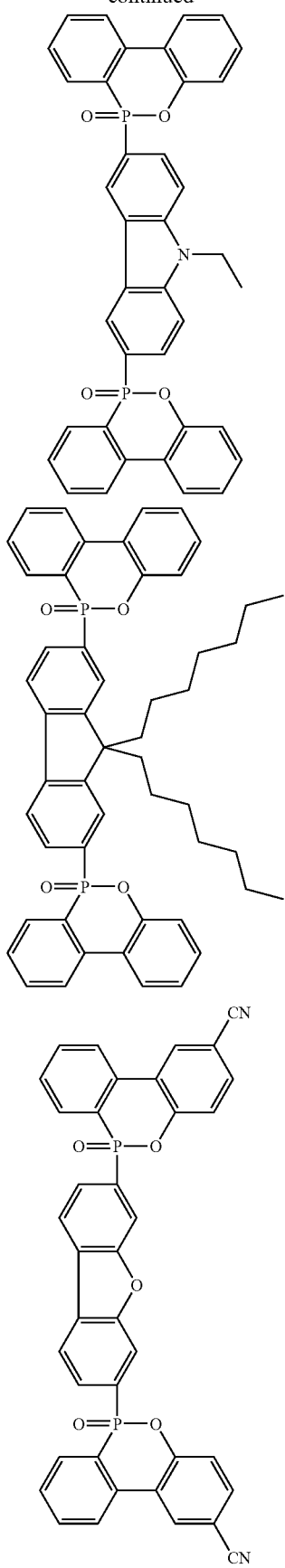
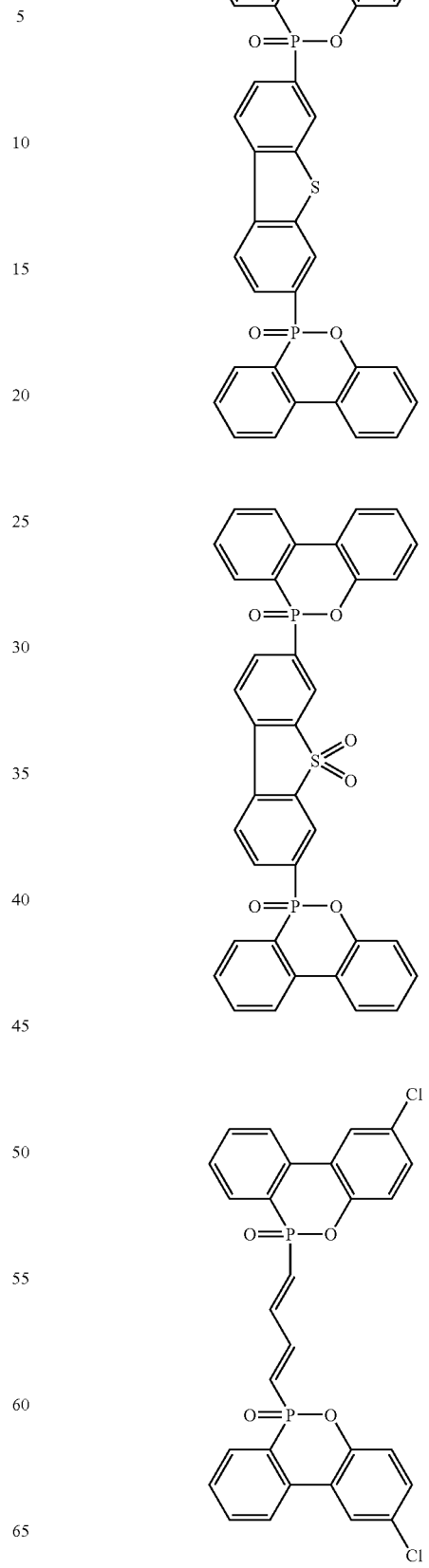

21
-continued
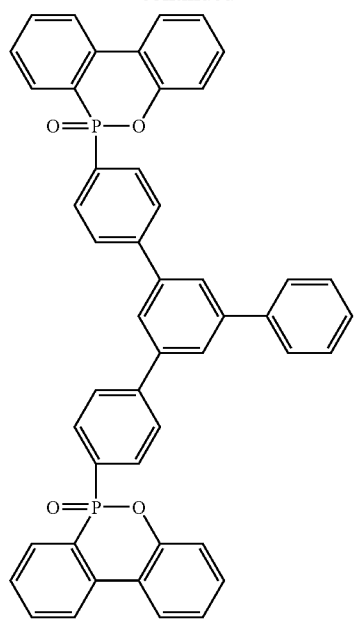
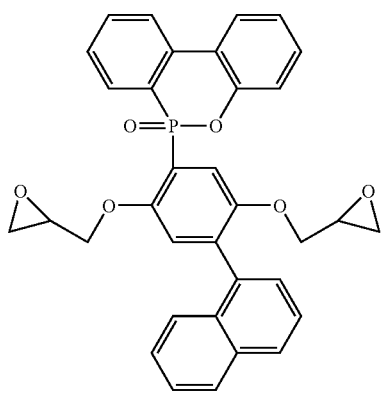
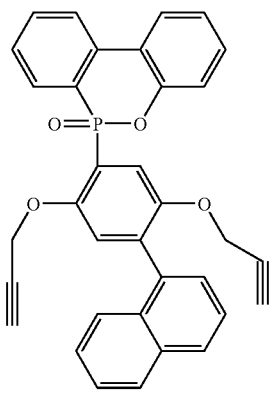
22
-continued
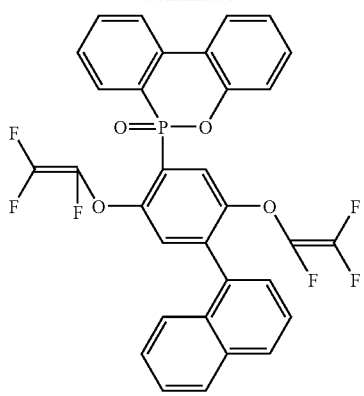
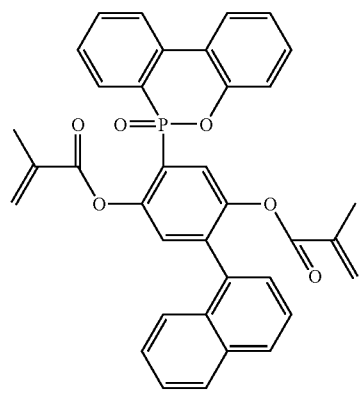
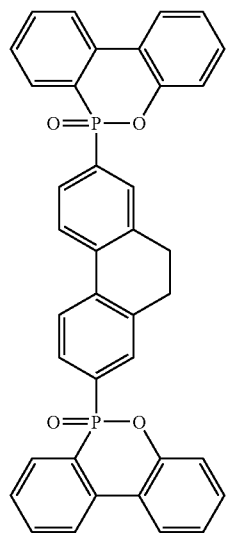

23
-continued
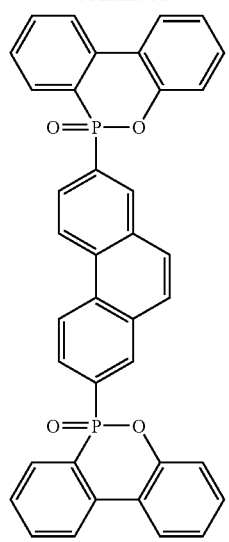
24
-continued
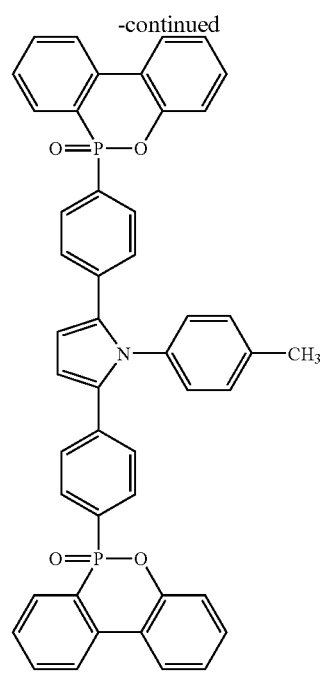
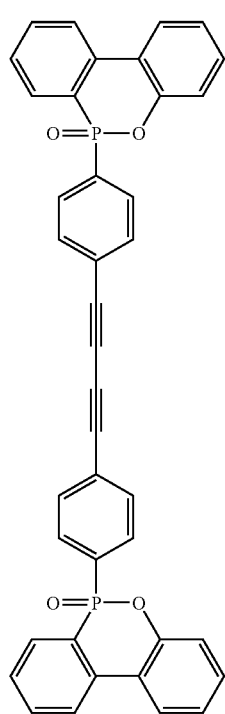
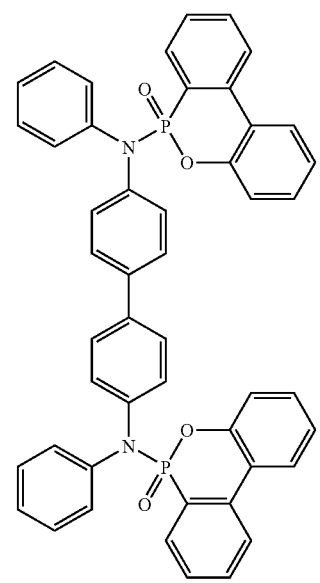

-continued
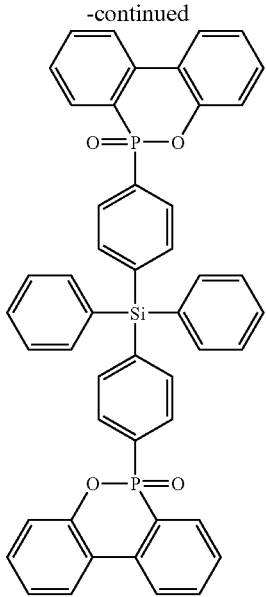
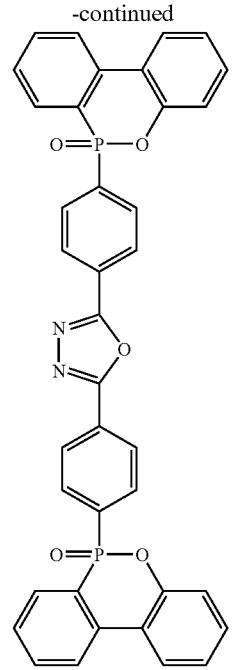
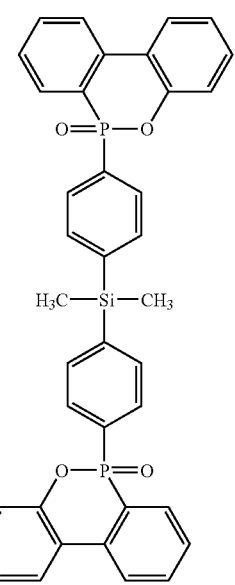
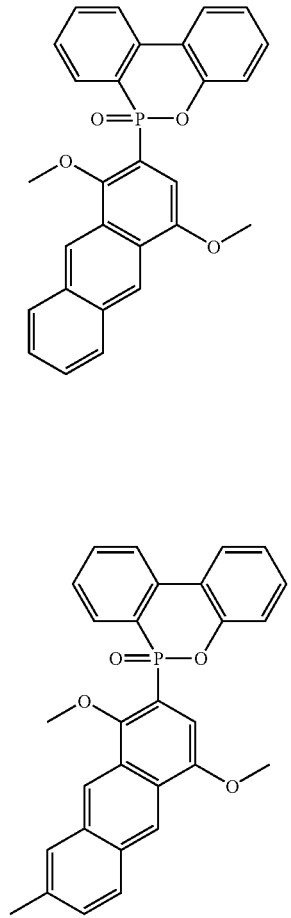

-continued

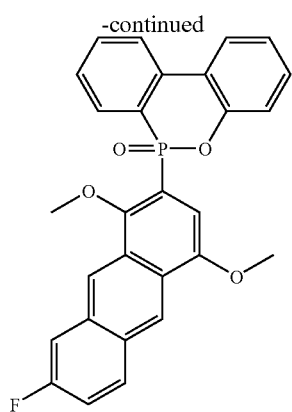
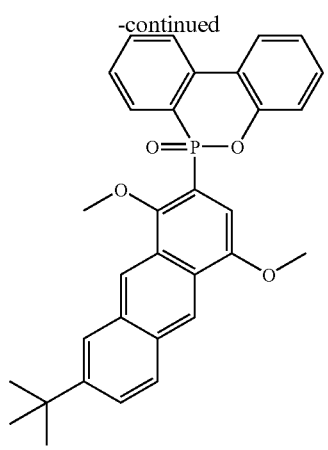

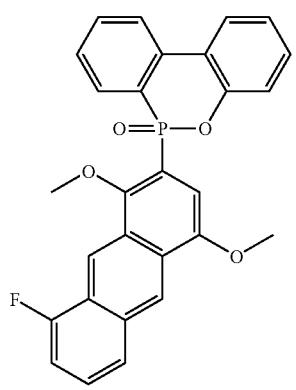
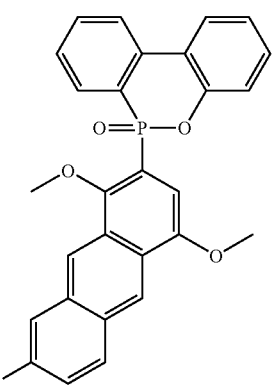

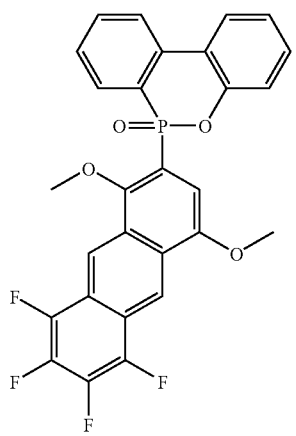
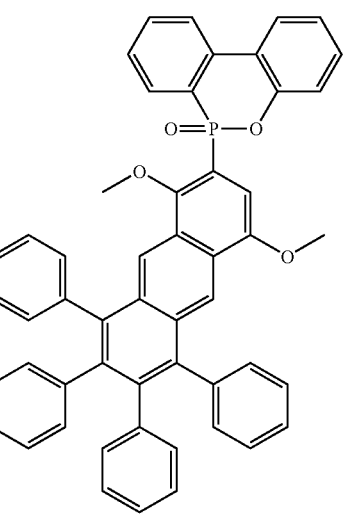

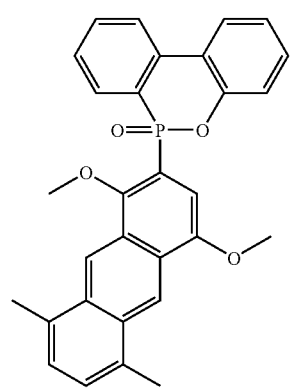

Advantageous Effects

Also, the present invention provides an organic EL diode wherein the electron transporting layer, the light emitting layer, and the light emitting/electron transporting layer include the phosphaphenanthrene compounds represented by the chemical formula 1. The phosphaphenanthrene compounds represented by the chemical formula 1 are useful as electron transporting materials or light emitting materials. In particular, the phosphaphenanthrene compounds according to the present invention are useful as electron transporting materials. Therefore, the OLED wherein the electron transporting layer or the light emitting layer includes the phosphaphenanthrene compounds according to the present invention can be driven at low power and can maintain the light emitting efficiency even when it is driven for a long time, making it possible to achieve the long lifetime of the OLED.

Meanwhile, in preparing the phosphaphenanthrene compounds represented by the chemical formula 1 of the present invention, any known methods can be used when the structure of final materials is the same, including the method described herein. In other words, solvent, reaction temperature, concentration, or catalyst, or the like, for preparing the phosphaphenanthrene compounds represented by the chemical formula 1 of the present invention are not specially limited and have nothing to do with preparing yield. For example, a reaction formula 1 will be described in detail.

In the case of the reaction formula 1, derivatives in a phenol form are synthesized by an addition reaction of phosphaphenanthrene derivatives to quinone. In order to make the synthesized derivatives into halogenated methyl, hydroxy group is alkoxylated. The halogenated methyl reacts with the triphenyl phosphonium so that it is synthesized as precursor capable of performing Wittig reaction. Monomers used in the Wittig reaction, which are generally phosphonium salt and phenyl aldehyde derivatives, react with strong base catalyst, such as sodium or alkyl lithium, using organic solvent, such as tetrahydrofuran.

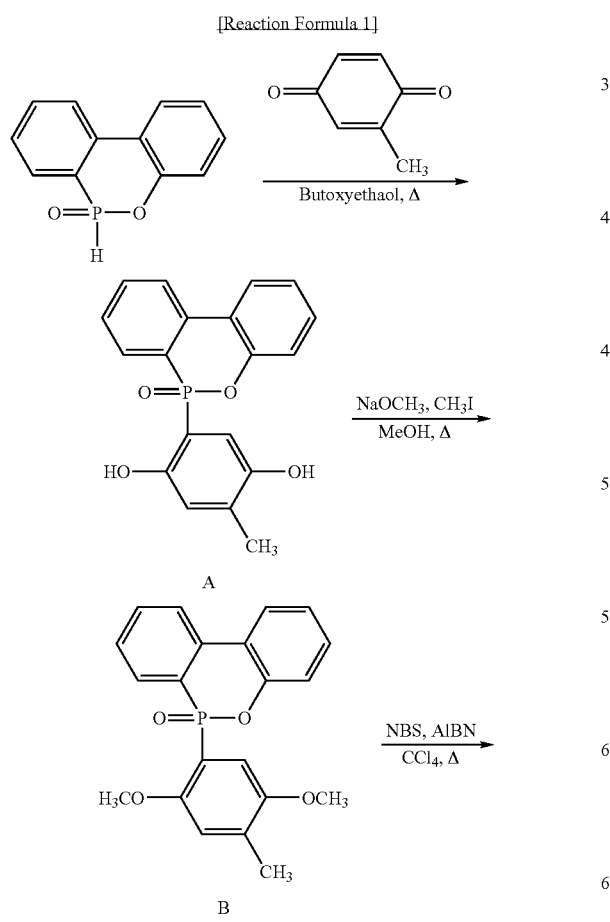

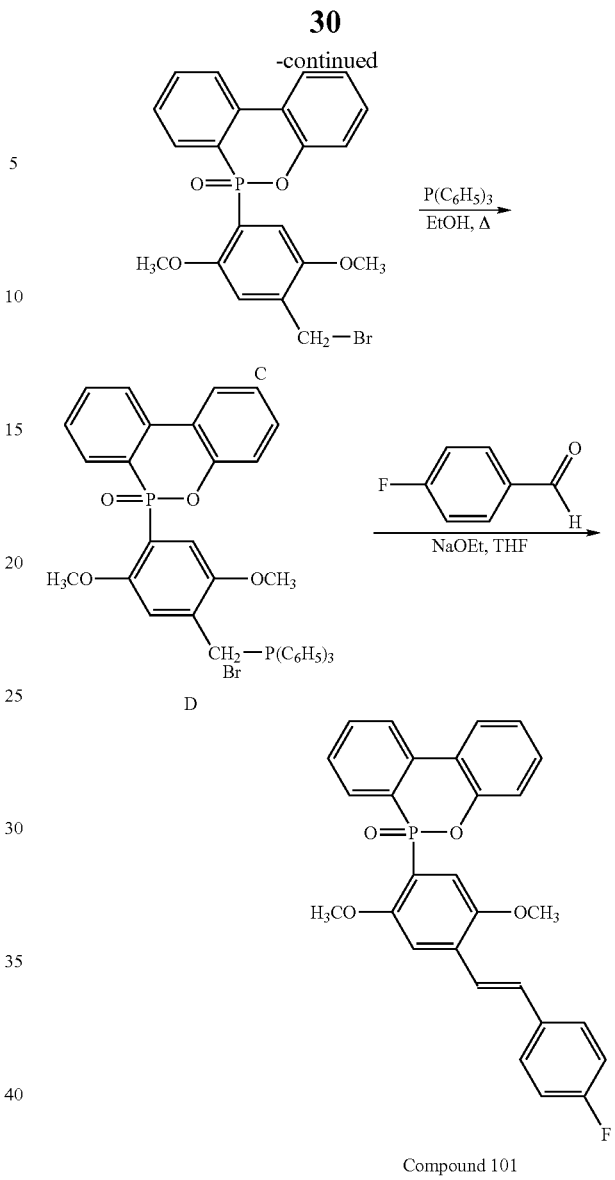

Compound 101

DESCRIPTION OF DRAWINGS

The above and other objects, features and advantages of the present invention will become apparent from the following description of preferred embodiments given in conjunction with the accompanying drawings, in which.

BEST MODE

Figure 1:
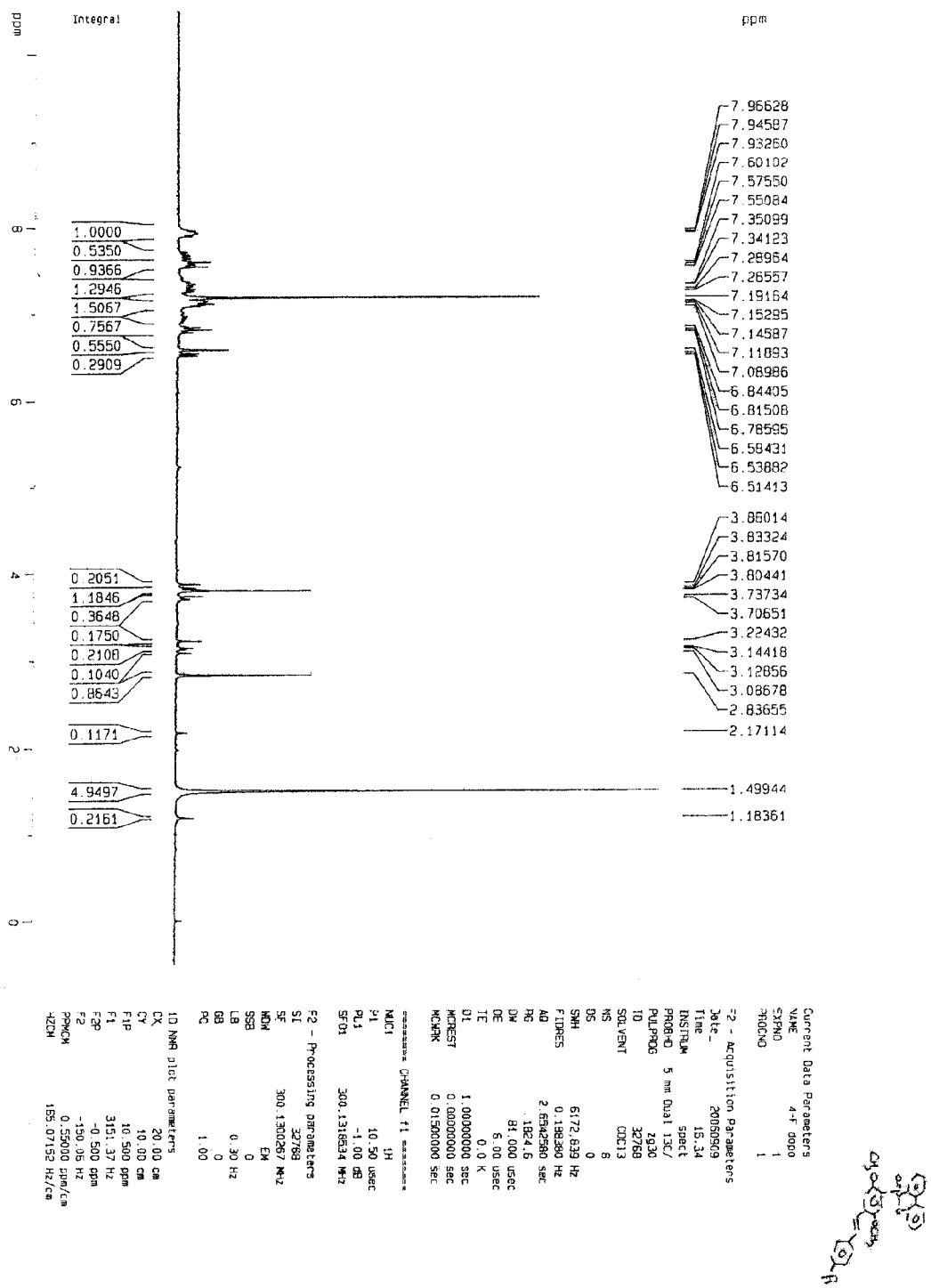
FIG. 1 is a $^1$H-NMR spectrum of compound 101 prepared according to a first embodiment.
Figure 2:
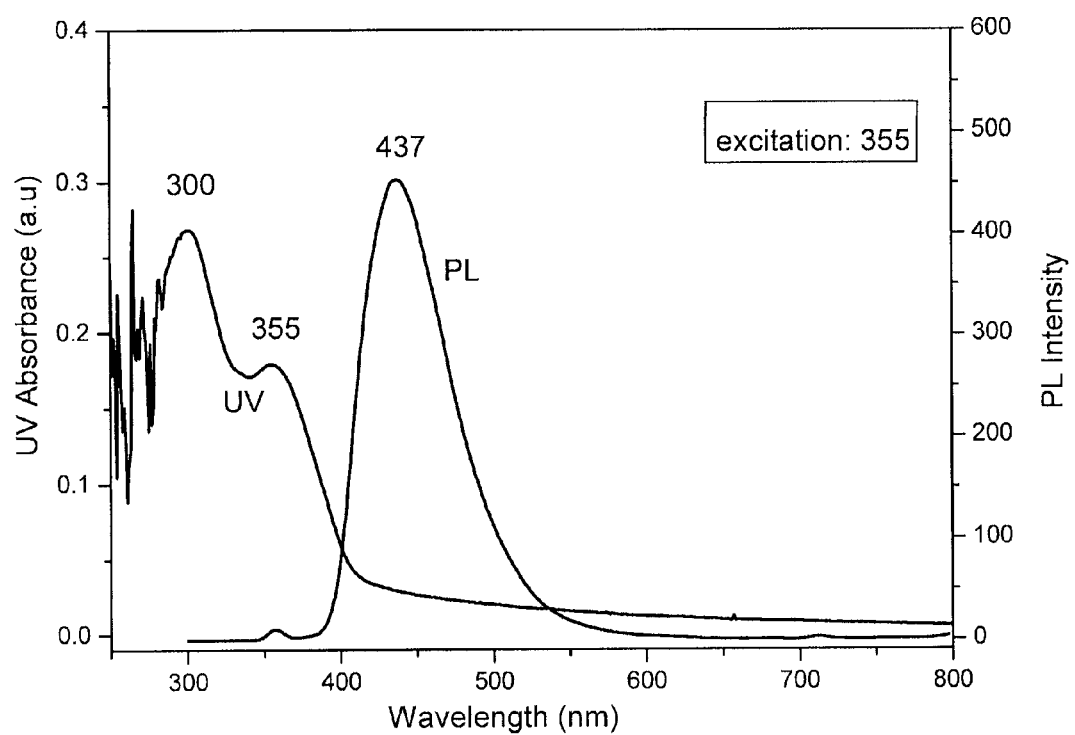
FIG. 2 is ultraviolet absorption (UV-vis) and photoluminescence (PL) spectrums of an OLED to which the compound 101 prepared according to the first embodiment is applied.
Figure 3:
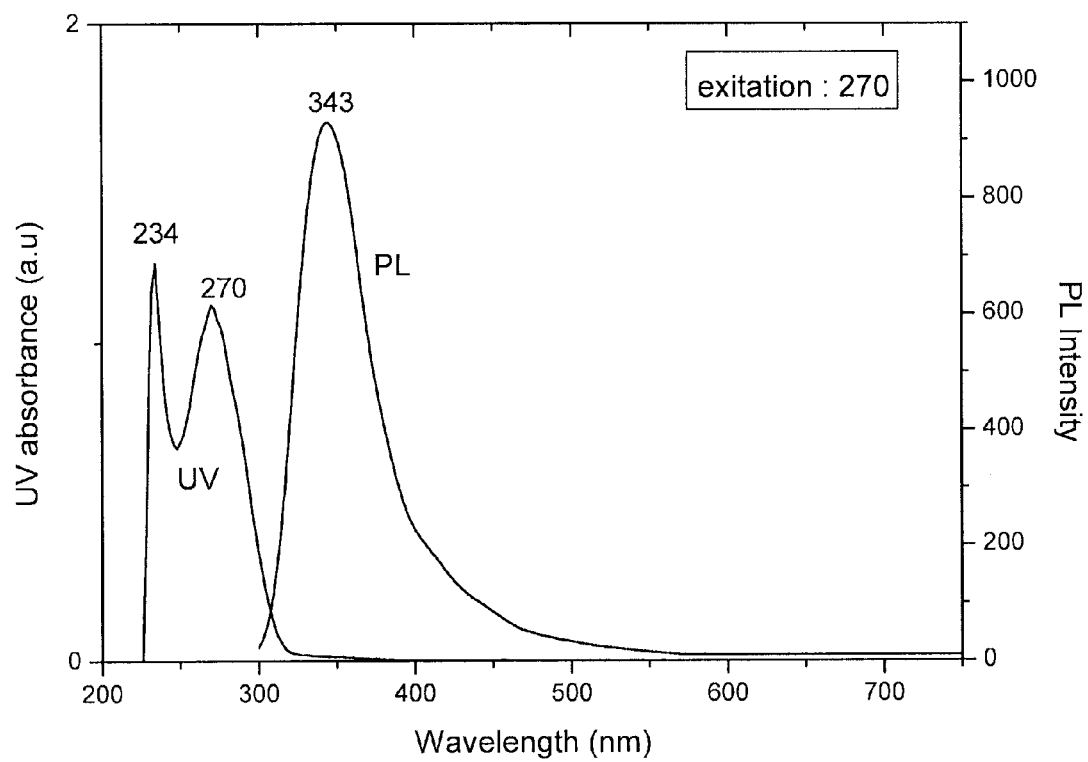
FIG. 3 is ultraviolet absorption (UV-vis) and photoluminescence (PL) spectrums of an OLED to which compound 108 prepared according to a eighth embodiment is applied.
Figure 4:
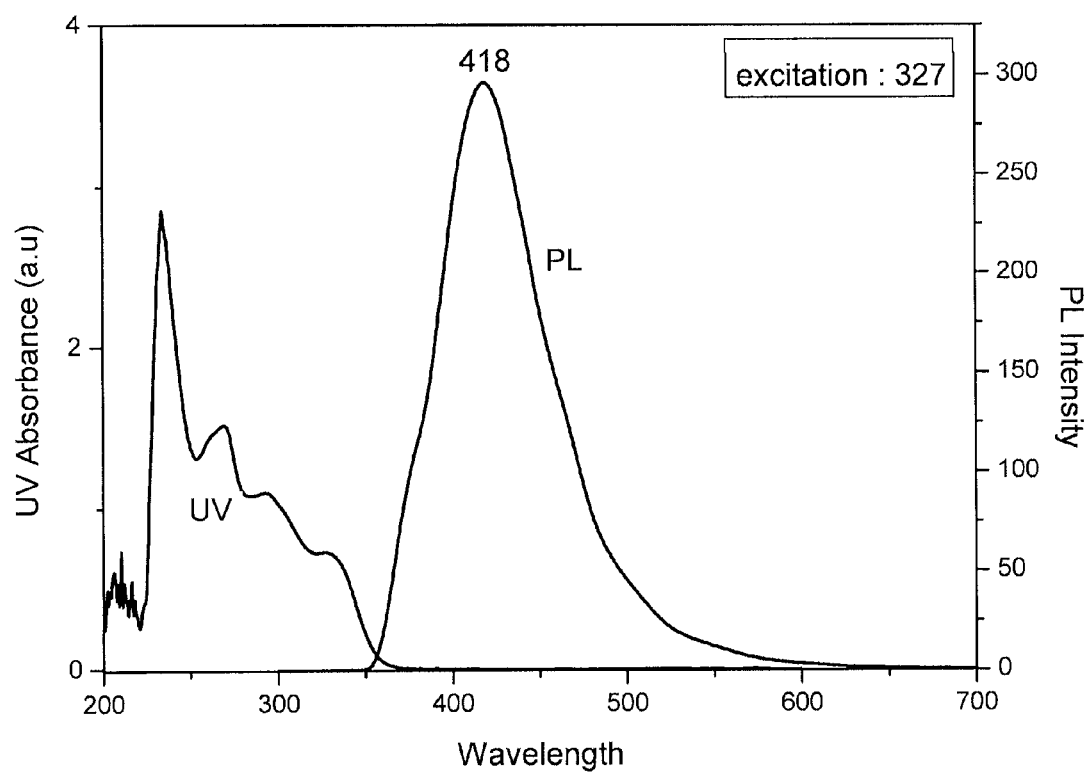
FIG. 4 is ultraviolet absorption (UV-vis) and photoluminescence (PL) spectrums of an OLED to which compound 109 prepared according to a ninth embodiment is applied.
Figure 5:
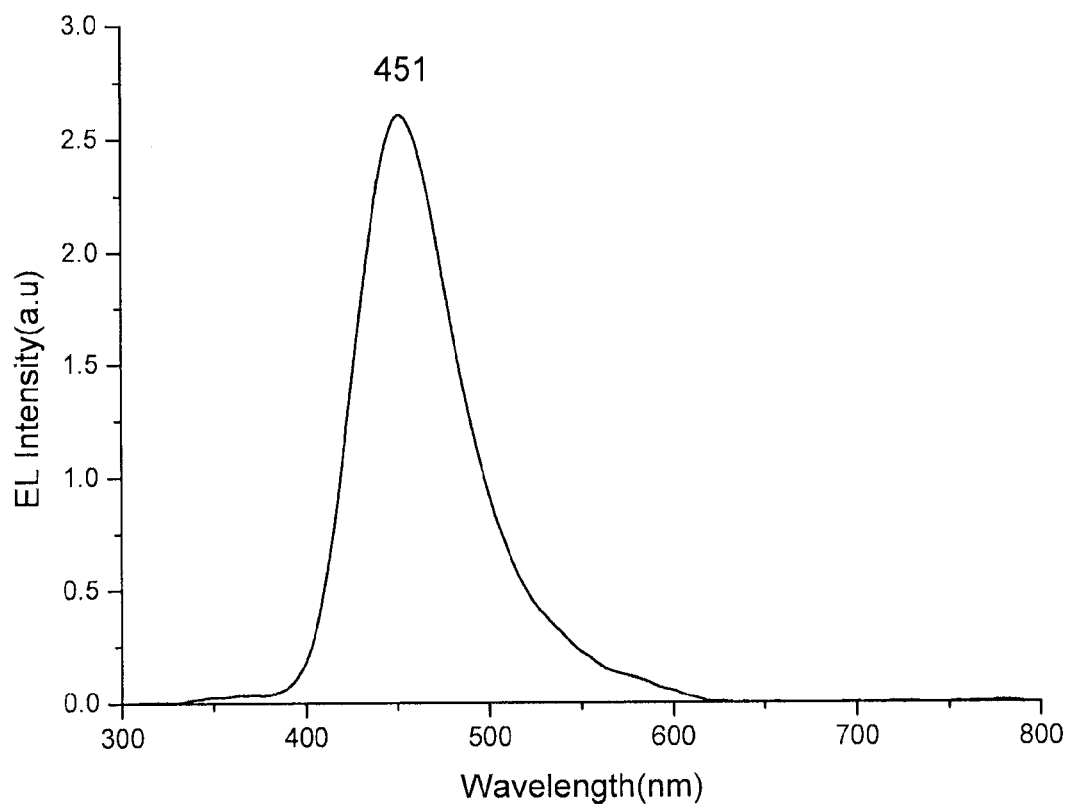
FIG. 5 is an electroluminescence (EL) spectrum of the OLED to which the compound 101 prepared according to the first embodiment is applied.
Figure 6:
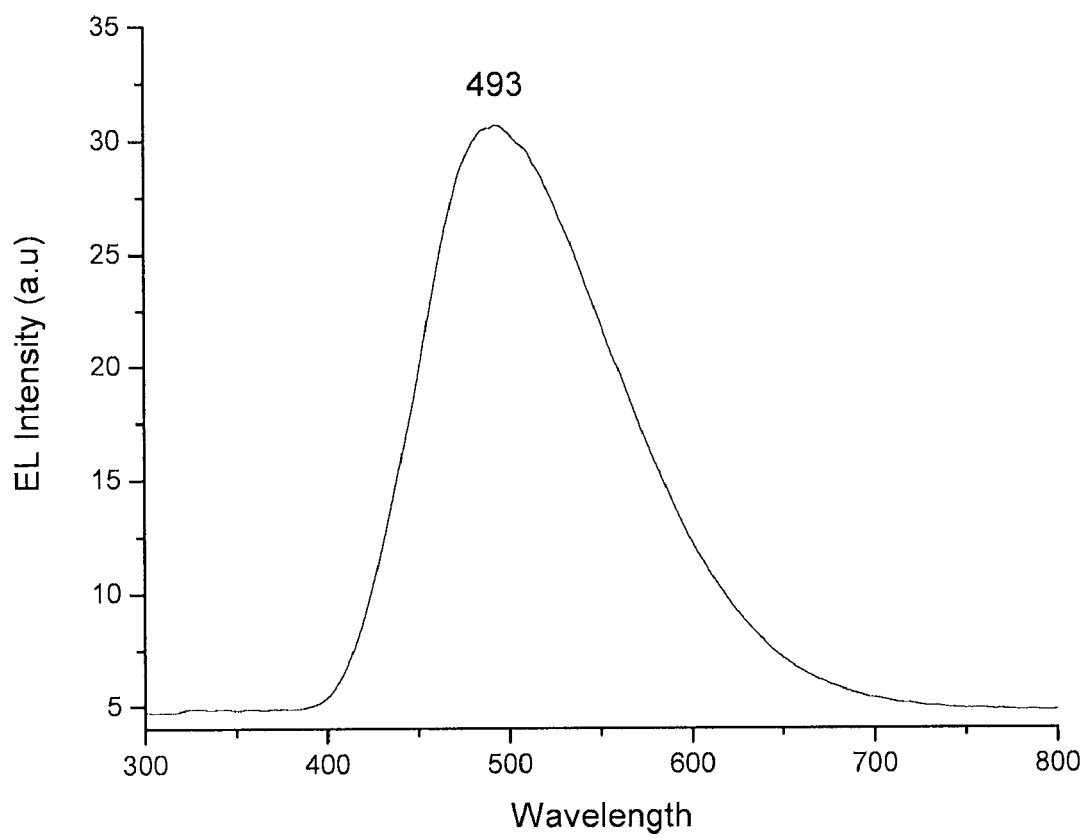
FIG. 6 is an electroluminescence (EL) spectrum of the OLED to which the compound 108 prepared according to the eighth embodiment is applied.
Figure 7:
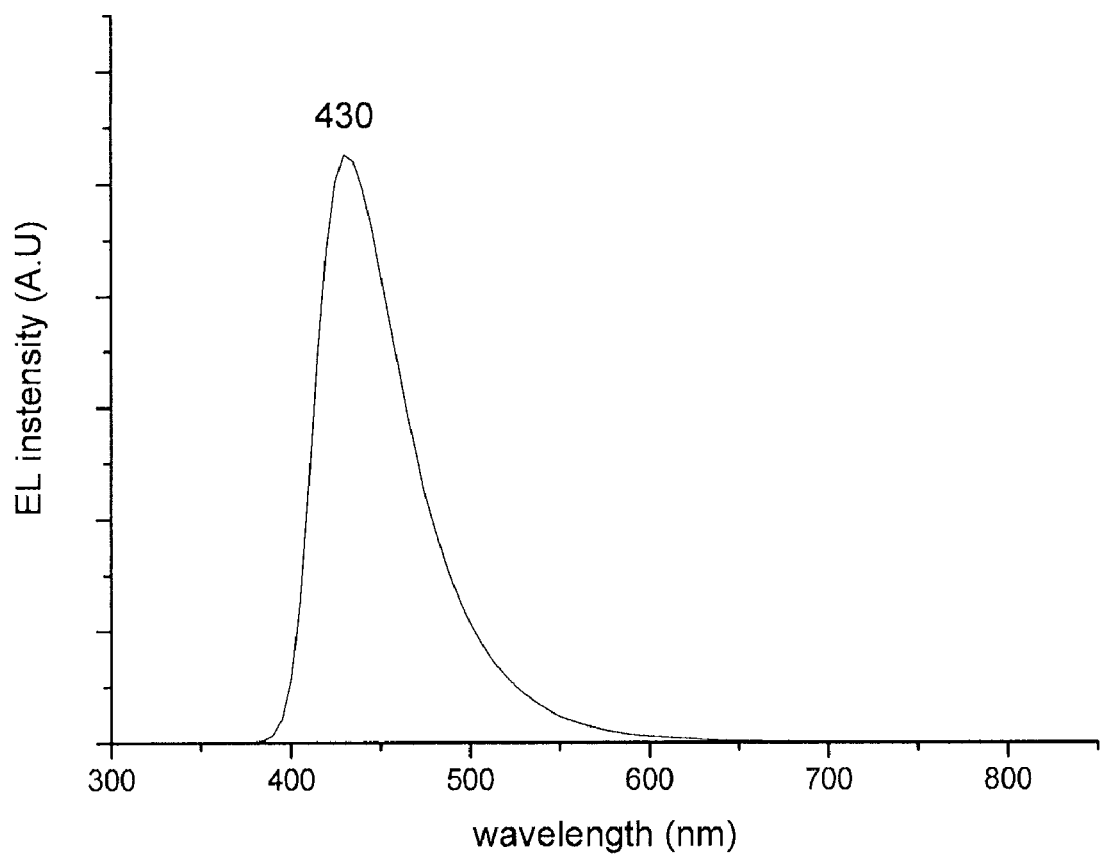
FIG. 7 is an electroluminescence (EL) spectrum of the OLED to which the compound 109 prepared according to the ninth embodiment is applied

Hereinafter, a method of preparing new phosphaphenanthrene compounds according to the present invention will be described with reference to embodiments of the present invention. However, the following embodiments are provided to help understanding of the present invention and therefore, the scope of the present invention is not limited to the embodiments.

First Embodiment

Synthesis of 10-{4'-[2-(4-fluorophenyl)-vinyl]-2',5'-dimethoxyphenyl}-9-oxa-10-phosphaphenanthrene-10-oxide (compound 101)

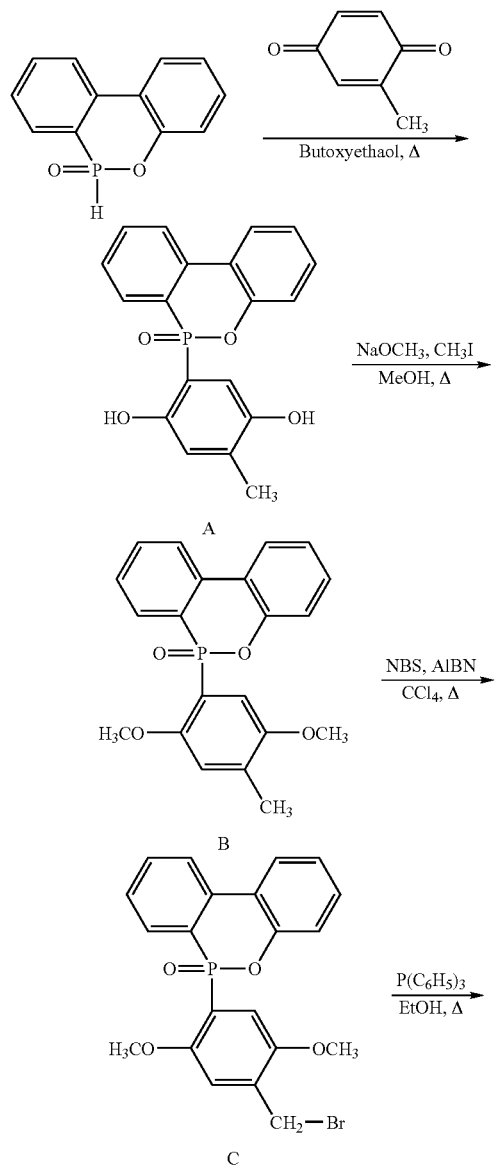

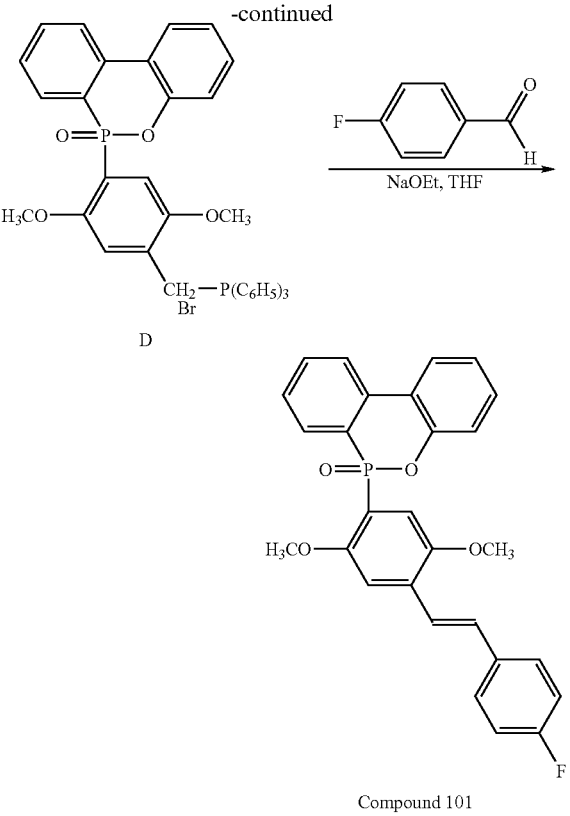

Compound 101

Synthesis of 10-(4'-methyl-2',5'-dihydroxyphenyl)-9,10-dihydro-9-oxa-10-phosphaphenanthrene-10-oxide (compound A)

9,10-dihydroxy-9-oxa-10-phosphaphenanthrene-10-oxide 200 g (0.93 mol), methyl-1,4-benzoquinone 107 g (0.88 mol), and 2-butoxyethanol 300 ml are put in a 1000 ml single round bottom flask under argon atmosphere and are then heated and recirculated for 12 hours. After the reaction is completed, they are slowly cooled at a normal temperature to produce precipitates. The precipitates are filtrated under reduced pressure using methanol to obtain targeted compound, that is, 10-(4'-methyl-2',5'-dihydroxyphenyl)-9,10-dihydro-9-oxa-10-phosphaphenanthrene-10-oxide (compound A) as a white solid 254 g (yield: 81%).

$^1$H NMR(CDCl$_3$), δ=2.15 (s, 3H, CH$_3$), 6.24 (d, 1H, aromatic), 6.75 (d, 1H, aromatic), 7.08~7.96 (m, 8H, aromatic)

Synthesis of 10-(4'-methyl-2',5'-dimethoxyphenyl)-9,10-dihydro-9-oxa-10-phosphaphenanthrene-10-oxide (compound B)

During 10-(4'-methyl-2',5'-dihydroxyphenyl)9,10-dihydro-9-oxa-10-phosphaphenanthrene-10-oxide (compound A) 20 g (0.06 mol) and methanol 200 ml are put and stirred in a 500 ml single round bottom flask under argon atmosphere, sodium methoxide 7 g (0.13 mol) and iodomethane 83 g (0.59 mol) are sequentially put in the flask. Thereafter, they are heated and recirculated for 4 hours. After the reaction is completed, methanol 100 ml is further added thereto and ethyl acetate is extracted by 200 ml three times. The extracted filtrates are washed two times with distilled water, is dried using magnesium sulfate anhydride, and are then filtrated under reduced pressure to obtain targeted compound, that is, 10-(4'-methyl-2',5'-dimethoxyphenyl)-9,10-dihydro-9-oxa-10-phosphaphenanthrene-10-oxide (compound B) as a white solid 12.6 g (yield: 58%).

$^1$H NMR(CDCl$_3$), δ=2.17 (s, 3H, CH$_3$), 3.14 (s, 3H, OCH$_3$), 3.81 (s, 3H, OCH$_3$), 6.56 (d, 1H, aromatic), 7.03-7.94 (m, 9H, aromatic)

Synthesis of 10-(4'-bromomethyl-2',5'-dimethoxyphenyl)-9,10-dihydro-9-oxa-10-phosphaphenanthrene-10-oxide (compound C)

During 10-(4'-methyl-2',5'-dimethoxyphenyl)-9,10-dihydro-9-oxa-10-phosphaphenanthrene-10-oxide (compound B) 1 g (27 mmol) and tetrachloromethane 20 ml are put and stirred in a 100 ml single round bottom flask under argon atmosphere, AIBN 0.02 g (1.08 mmol) and N-bromosuccinimide 0.97 g (54 mmol) are sequentially put in the flask. Thereafter, they are then heated and recirculated for 12 hours. After the reaction is completed, dichloromethane 80 ml is further added thereto, is washed two times with distilled water, is dried using magnesium sulfate anhydride, and then filtrated under reduced pressure to obtain a brown solid 1.23 g. This is separated from a by-product using developing solution (ethyl acetate/N-hexane: 1/2) by quick chromatography to obtain targeted compound, that is, 10-(4'-bromomethyl-2', 5'-dimethoxyphenyl)-9,10-dihydro-9-oxa-10-phosphaphenanthrene-10-oxide (compound C) as a white solid 0.42 g (yield:33%).

$^1$H NMR(CDCl$_3$), δ=3.14 (s, 3H, OCH$_3$), 3.86 (s, 3H, OCH$_3$), 4.41 (s, 3H, CH$_2$Br), 6.72 (d, 1H, aromatic), 7.08-7.95 (m, 9H, aromatic)

Synthesis of 10-(4'-triphenyl phosphonium bromide-2',5'-dimethoxyphenyl)-9,10-dihydro-9-oxa-10-phosphaphenanthrene-10-oxide (compound D)

10-(4'-bromomethyl-2',5'-dimethoxyphenyl)-9,10-dihydro-9-oxa-10-phosphaphenanthrene-10-oxide (compound C) 14.85 g (0.03 mol) and ethanol 100 mg are put and stirred in a 500 ml single round bottom flask and triphenylphosphine 10.26 g (0.04 mol) are then put in the flask. Thereafter, they are heated and recirculated for 4 hours. After the reaction is completed, they are slowly cooled at a normal temperature. Precipitates produced after the cooling are filtered using diethyl ether to obtain targeted compound, that is, 10-(4'-triphenyl phosphonium bromide-2',5'-dimethoxyphenyl)-9,10-dihydro-9-oxa-10-phosphaphenanthrene-10-oxide (compound D) as a white solid 23.31 g (yield:99%).

$^1$H NMR(CDCl$_3$), δ=3.14 (s, 3H, OCH$_3$), 3.26 (s, 3H, OCH$_3$), 5.15 (t, 1H, CH$_2$P), 5.67 (t, 1H, CH$_2$P), 7.16-8.00 (m, 15H, aromatic)

Synthesis of 10-{4'-[2-(4-fluorophenyl)-vinyl]-2',5'-dimethoxyphenyl}-9-oxa-10-phosphaphenanthrene-10-oxide (compound 101)

After 10-(4'-triphenyl phosphonium bromide-2',5'-dimethoxyphenyl)-9,10-dihydro-9-oxa-10-phosphaphenanthrene-10-oxide (compound D) 5 g (69.6 mmol), 4-fluoro benzaldehyde 0.95 g (76.6 mmol), and tetrahydrofuran anhydride 50 ml are put and stirred in a 100 ml single round bottom flask under argon atmosphere, 21%-sodium ethoxide 3.3 ml (21% ethanol solution, 83.5 mml) is slowly dropped thereinto. They are stirred at a normal temperature for 2 hours. After the reaction is completed, they are evaporated under reduced pressure. This mixture is obtained as targeted compound, that is, a white solid 2.92 g (yield:89%) of 10-{4'-[2-(4-fluorophenyl)-vinyl]-2',5'-dimethoxyphenyl}-9-oxa-10-phosphaphenanthrene-10-oxide (compound 101) using developing solution (ethyl acetate/N-hexane: 1/1).

$^1$H NMR(CDCl$_3$), δ=2.83 (s, 3H, OCH$_3$), 3.80 (s, 3H, OCH$_3$), 6.51~7.96 (m, 16H, vinyl and aromatic)

Second Embodiment

Synthesis of 10-{4'-[2-(naphthalene)-vinyl]-2',5'-dimethoxyphenyl}-9-oxa-10-phosphaphenanthrene-10-oxide (compound 102)

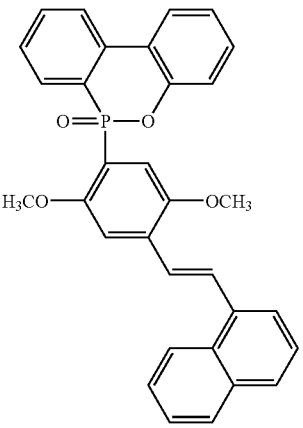 [SMILES: COc1cc(P2(=O)Oc3ccccc3-c3ccccc32)c(OC)cc1/C=C/c1cccc2ccccc12]

Compound 102

After 10-(4'-triphenyl phosphonium bromide-2',5'-dimethoxyphenyl)-9,10-dihydro-9-oxa-10-phosphaphenanthrene-10-oxide (compound D) 1 g (69.6 mmol), 1-naphthylaldehyde 0.21 g (13.9 mmol), and tetrahydrofuran anhydride 50 ml are put and stirred in a 100 ml single round bottom flask under argon atmosphere, 21%-sodium ethoxide 3.3 ml (21% ethanol solution, 83.5 mml) is slowly dropped thereinto. They are stirred at a normal temperature for 2 hours. After the reaction is completed, they are evaporated under reduced pressure. This mixture is obtained as targeted compound, that is, a white solid 0.39 g (yield:56%) of 10-{4'-[2-(naphthalene)-vinyl]-2',5'-dimethoxyphenyl}-9-oxa-10-phosphaphenanthrene-10-oxide (compound 102) using developing solution (ethyl acetate/N-hexane:1/1).

$^1$H NMR(CDCl$_3$), δ=2.83 (s, 3H, OCH$_3$), 3.80 (s, 3H, OCH$_3$), 6.51~7.96 (m, 19H, vinyl and aromatic)

Third Embodiment

Synthesis of 10-{4'-[2-(cyanophenyl)-vinyl]-2',5'-dimethoxyphenyl}-9-oxa-10-phosphaphenanthrene-10-oxide (compound 103)

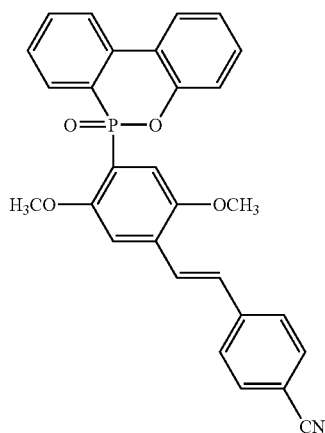 [SMILES: COc1cc(P2(=O)Oc3ccccc3-c3ccccc32)c(OC)cc1/C=C/c1ccc(C#N)cc1]

Compound 103

After 10-(4'-triphenyl phosphonium bromide-2',5'-dimethoxyphenyl)-9,10-dihydro-9-oxa-10-phosphaphenanthrene-10-oxide (compound D) 1 g (14 mmol), 4-cyano benzaldehyde 0.2 g (15.4 mmol), and tetrahydrofuran anhydride 30 ml are put and stirred in a 50 ml single round bottom flask under argon atmosphere, 21%-sodium ethoxide 0.66 ml (21% ethanol solution, 16.8 mml) is slowly dropped thereinto. They are stirred at a normal temperature for 2 hours. After the reaction is completed, they are evaporated under reduced pressure. This mixture is obtained as targeted compound, that is, a white solid 0.42 g (yield:65%) of 10-{4'-[2-(4-cyanophenyl)-vinyl]-2',5'-dimethoxyphenyl}-9-oxa-10-phosphaphenanthrene-10-oxide (compound 103) using developing solution (ethyl acetate/N-hexane: 1/1).

$^1$H NMR(CDCl$_3$), δ=3.30 (s, 3H, OCH$_3$), 3.94 (s, 3H, OCH$_3$), 6.92-7.93 (m, 16H, vinyl and aromatic)

Fourth Embodiment

Synthesis of 10-{4'-[2-(3-phenylvinyl]-2',5'-dimethoxyphenyl}-9-oxa-10-phosphaphenanthrene-10-oxide)-vinyl]-2',5' dimethoxyphenyl}-9-oxa-10-phosphaphenanthrene-10-oxide (compound 104)

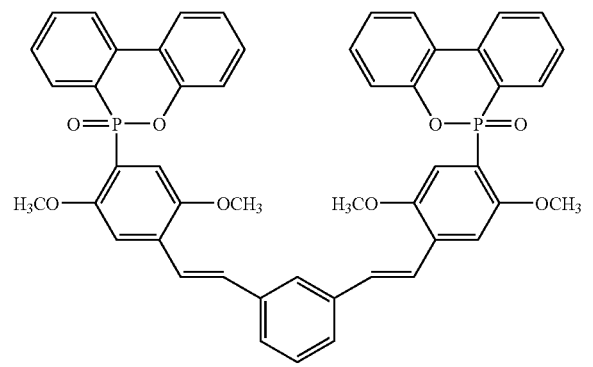 [SMILES: COc1cc(P2(=O)Oc3ccccc3-c3ccccc32)c(OC)cc1/C=C/c1cccc(/C=C/c2cc(OC)c(P3(=O)Oc4ccccc4-c4ccccc43)cc2OC)c1]

Compound 104

After 10-(4'-triphenyl phosphonium bromide-2',5'-dimethoxyphenyl)-9,10-dihydro-9-oxa-10-phosphaphenanthrene-10-oxide (compound D) 1 g (14 mmol), benzene 1,3-carbaldehyde 0.1 g (15.4 mmol), and tetrahydrofuran anhydride 50 ml are put and stirred in a 50 ml single round bottom flask under argon atmosphere, 21%-sodium ethoxide 0.66 ml (21% ethanol solution, 16.8 mml) is slowly dropped thereinto. They are stirred at a normal temperature for 2 hours. After the reaction is completed, they are evaporated under reduced pressure. This mixture is obtained as targeted compound, that is, a white solid 0.23 g (yield:20%) of 10-{4'-[2-(3-phenylvinyl]-2',5'-dimethoxyphenyl}-9-oxa-10-phosphaphenanthrene-10-oxide)-vinyl-2',5'-dimethoxyphenyl}-9-oxa-10-phosphaphenanthrene-10-oxide (compound 104) using developing solution (ethyl acetate/N-hexane: 1/1).

$^1$H NMR(CDCl$_3$), δ=3.22 (s, 3H, OCH$_3$), 3.70 (s, 3H, OCH$_3$), 6.40~7.96 (m, 28H, vinyl and aromatic)

Fifth Embodiment

Synthesis of 10-{4'-[2-(FIrpic)]-2',5'-dimethoxyphenyl}-9-oxa-10-phosphaphenanthrene-10-oxide (compound 105)

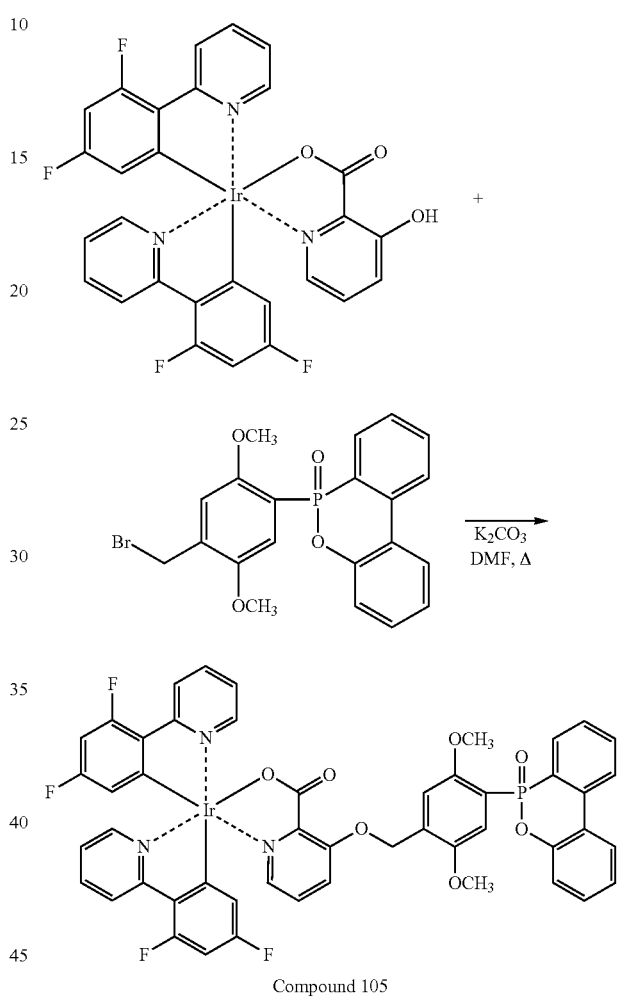

Compound 105

FIrpic alcohol 0.72 g (0.11 mmol) and 10-(4'-bromomethyl-2',5'-dimethoxyphenyl)-9,10-dihydro-9-oxa-10-phosphaphenanthrene-10-oxide 0.5 g (0.11 mmol) are mixed with dimethylformamide 15 ml in a 100 ml flask and potassium carbonate 0.46 g (0.33 mmol) is put in the flask. After the addition, they are reacted by heat and recirculation at 100° C. for 48 hours. After the reaction, dichloro methane 100 ml is added thereto and is then washed with water to produce filtrates. Water in the filtrates is removed by magnesium sulfate. The dichloro methane is removed and concentrated under reduced pressure to obtain targeted compound, that is, 10-{4'-[2-(FIrpic)]-2',5'-dimethoxyphenyl}-9-oxa-10-phosphaphenanthrene-10-oxide (compound 105) as a yellow solid 0.98 g (yield: 81%).

$^1$H NMR(CDCl$_3$), δ=3.24 (s, 3H, OCH$_3$), 3.71 (s, 3H, OCH$_3$), 4.52 (s, 2H, CH$_2$), 6.40-7.96 (m, 27H, vinyl and aromatic)

Sixth Embodiment

Synthesis of 10-biphenyl-(4-(9-oxa-10-phosphaphenanthrene)-9-oxa-10-phosphaphenanthrene 10-oxide (compound 106)

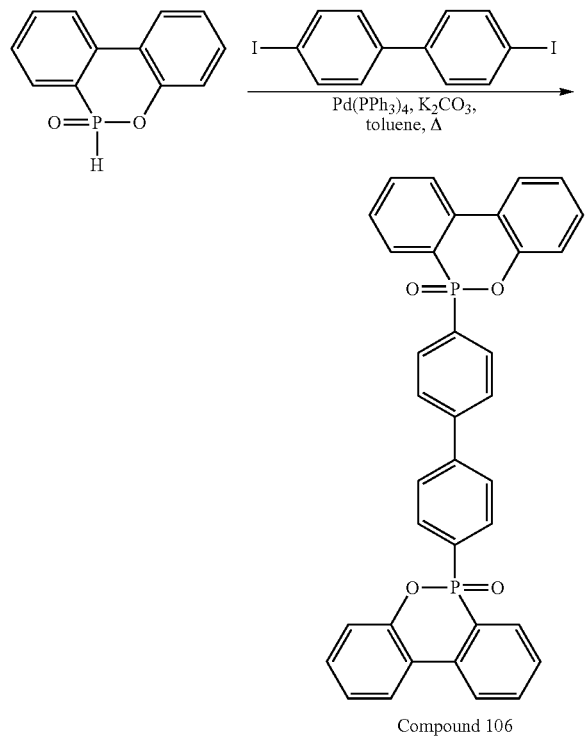

Compound 106

9,10-dihydroxy-9-oxa-10-phosphaphenanthrene-10-oxide 10 g (0.05 mol), potassium carbonate 6.4 g (0.05 mol), 4-4'-iodobiphenyl 9.38 g (0.023 mol), palladium catalyst 1.6 g (23 mol), and dioxane 60 ml are put in a 100 ml single round bottom flask under argon atmosphere. They are heated and recirculated for hours. After the reaction is completed, they are slowly cooled at a normal temperature, are distilled under reduced pressure, are dissolved in dichloro methane solution, and are washed with distilled water several times. They are dried and filtered by magnesium sulfate to remove and concentrate solvent under reduced pressure and is purified by silica gel column chromatography method (ethyl acetate:hexane=1:1) to obtain targeted compound, that is, 10-biphenyl-(4-(9-oxa-10-phosphaphenanthrene)-9-oxa-10-phosphaphenanthrene 10-oxide (compound 106) as a white solid 18.32 g (yield:68%)

$^1$H NMR(CDCl$_3$), δ=6.56 (d, 1H, aromatic), 7.01-7.99 (m, 23H, aromatic)

Seventh Embodiment

Synthesis of 9,9-dihexyl-(2,7-(9-oxa-10-phosphaphenanthrene)-9-oxa-10-phosphaphenanthrene 10-oxide)fluorene (compound 107)

Compound 107

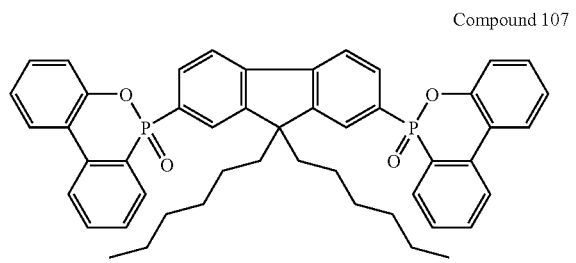

9,10-dihydroxy-9-oxa-10-phosphaphenanthrene-10-oxide 10 g (0.05 mol), potassium carbonate 6.4 g (0.05 mol), 4,4'-iodine 9,9-dihexyl fluorene 13.5 g (0.023 ml), palladium catalyst 1.6 g (23 mmol), and dioxane 100 ml are put in a 100 ml single round bottom flask under argon atmosphere. They are heated and recirculated for 48 hours. After the reaction is completed, they are slowly cooled at a normal temperature, are distilled under reduced pressure, are dissolved in dichloro methane solution, and are then washed with distilled water several times. This is dried and filtered by magnesium sulfate to remove and concentrate solvent under reduced pressure and is then purified by silica gel column chromatography method (ethyl acetate:hexane=1:1) to obtain targeted compound, that is, 9,9-dihexyl-(2,7-(9-oxa-10-phosphaphenanthrene)-9-oxa-10-phosphaphenanthrene 10-oxide) fluorene (compound 107) as a white solid 14.4 g (yield:40%)

$^1$H NMR(CDCl$_3$), δ=0.35~2.1 (m, 26H, dihexyl group), 7.05~8.29 (m, 22H, aromatic)

Eighth Embodiment

Synthesis of 10-(2-p-9-oxa-10-phosphaphenanthrene-vinyl)-9-oxa-10-phosphaphenanthrene 10-oxide (compound 108)

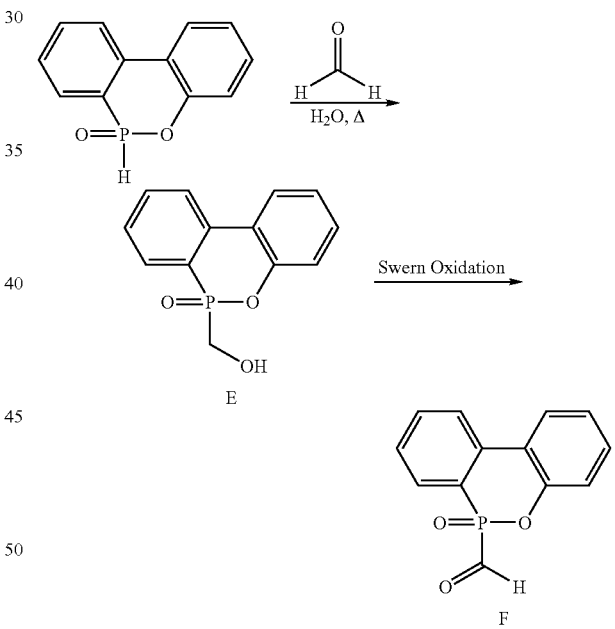

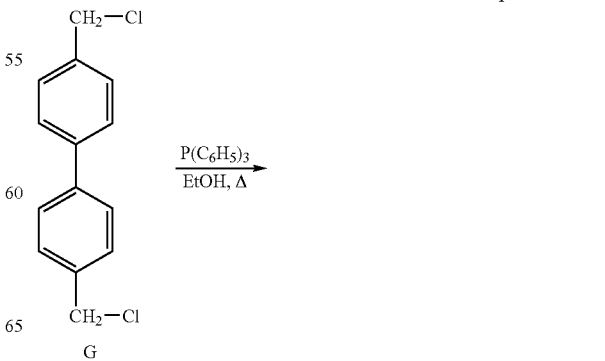

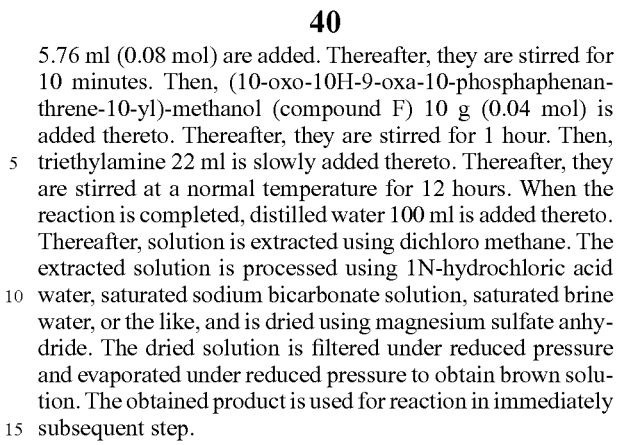

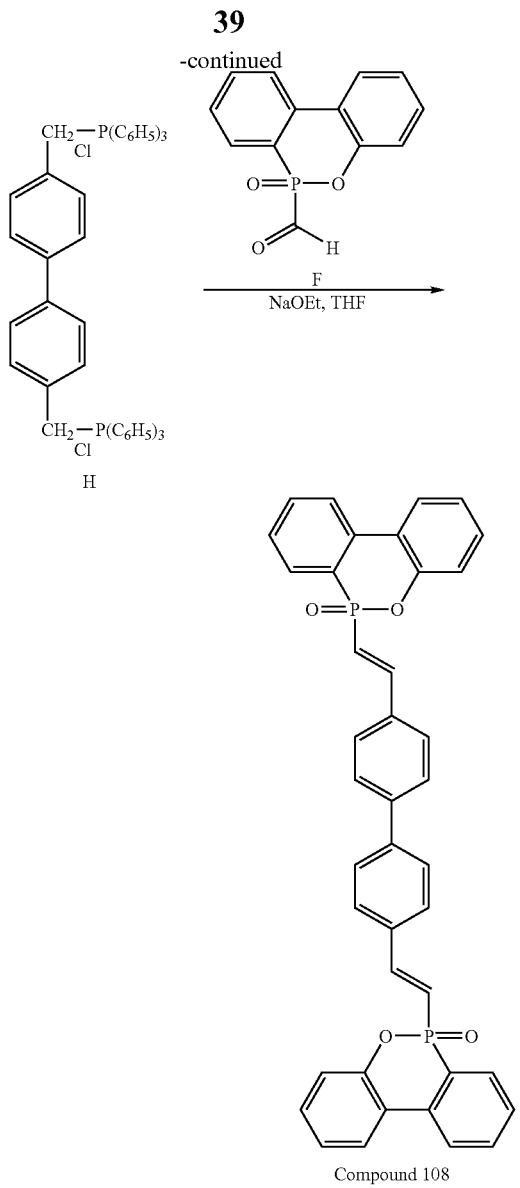

Compound 108

Synthesis of (10-oxo-10H-9-oxa-10-phosphaphenan-threne-10-yl)-methanol (compound E)

9-oxa-10-phosphaphenanthrene 10-oxide 20 g (0.09 mol) and paraformaldehyde 3.0 g (0.10 mol) are dissolved in distilled water 100 ml and are then heated and recirculated for 6 hours. After the reaction is completed, they are cooled at normal temperature and at the same time, is slowly added with diethyl ether to produce precipitates. The produced precipitates are filtered and dried in a reduced pressure oven to obtain targeted compound, that is, (10-oxo-10H-9-oxa-10-phosphaphenanthrene-10-yl)-methanol (compound E) as a white solid 20.3 g (yield: 89%).

Synthesis of (10-oxo-10H-9-oxa-10 phosphaphenanthrene-10-carbaldehyde (compound F)

Purified dichloro methane anhydride 100 ml is cooled using dry ice and acetone. When the cooling is completed, oxalyl chloride 42.5 ml (0.05 mol) and dimethyl sulfur oxide 5.76 ml (0.08 mol) are added. Thereafter, they are stirred for 10 minutes. Then, (10-oxo-10H-9-oxa-10-phosphaphenan-threne-10-yl)-methanol (compound F) 10 g (0.04 mol) is added thereto. Thereafter, they are stirred for 1 hour. Then, triethylamine 22 ml is slowly added thereto. Thereafter, they are stirred at a normal temperature for 12 hours. When the reaction is completed, distilled water 100 ml is added thereto. Thereafter, solution is extracted using dichloro methane. The extracted solution is processed using 1N-hydrochloric acid water, saturated sodium bicarbonate solution, saturated brine water, or the like, and is dried using magnesium sulfate anhydride. The dried solution is filtered under reduced pressure and evaporated under reduced pressure to obtain brown solution. The obtained product is used for reaction in immediately subsequent step.

Synthesis of 10-(2-p-9-oxa-10-phosphaphenan-threne-vinyl)-9-oxa-10-phosphaphenanthrene 10-oxide (compound 108)

The product 7.73 g (0.03 mol), phosphonium salt 12.7 g (0.02 mol), and tetrahydrofuran anhydride 100 ml are added to make suspension. Thereafter, they are stirred and at the same time, 21%-sodium ethoxide solution is dropped thereinto.

They are stirred for 24 hours after the dropping is completed. Thereafter, ethyl acetate 100 ml is added. Then, they are washed with distilled water several times. solution is dried using magnesium sulfate anhydride and filtered under reduced pressure and evaporated under reduced pressure to obtain a dark yellow solid. The produced solid is purified using ethyl acetate:hexane (1:1) developing solution to remove by-product, that is, triphenyloxide, thereby obtaining targeted compound, that is, 10-(2-p-9-oxa-10-phos-phaphenanthrene-vinyl)-9-oxa-10-phosphaphenanthrene 10-oxide (compound 108) as a white solid 6.42 g (yield: 32%).

$^1$H NMR(CDCl$_3$), δ=5.40 (d, 4H, vinyl), 6.88-8.89 (m, 24H, aromatic)

Ninth Embodiment

Synthesis of 10-{4'-[2-naphthyl]-2',5'-dimethoxyphe-nyl}-9-oxa-10-phosphaphenanthrene-10-oxide (compound 109)

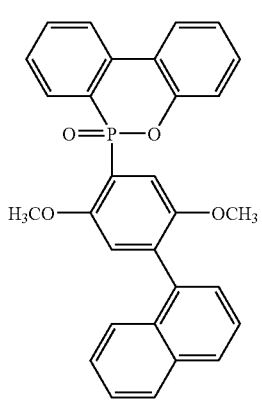

Compound 109

9,10-dihydroxy-9-oxa-10-phosphaphenanthrene-10-oxide 3.97 g (0.02 mol), 2-naphthyl-1,4-benzoquinone 4.05 g (0.02 mol), and 2-ethoxyethanol 10 ml are put in a 100 ml single round bottom flask under argon atmosphere. They are heated and recirculated for 12 hours. After the reaction is completed, they are slowly cooled at a normal temperature to produce precipitates. This precipitates are filtered under reduced pressure using methanol to obtain a powder 3.61 g of light color. This powder to which Iodomethane 4.5 g (0.03 mol), potassium carbonate 4.43 g (0.03 mol), acetone 50 ml are sequentially added is heated and circulated for 4 hours. After the reaction is completed, this is extracted using dichloro methane and distilled water. This is dried using magnesium sulfate anhydride and then filtered under reduced pressure to remove solvent, thereby obtaining targeted compound, that is, 10-{4'-[2-naphthyl]-2',5'-dimethoxyphenyl}-9-oxa-10-phosphaphenanthrene-10-oxide (compound 109) as a white solid 3.6 g (yield:44%).

$^1$H NMR(CDCl$_3$): δ=2.15 (s, 3H, OCH$_3$), 6.24 (d, 1H, aromatic), 6.75 (d, 1H, aromatic), 7.08-7.96 (m, 8H, aromatic)

Tenth Embodiment

Synthesis of 10-(1,4-dimethoxyanthracene-2-yl)-9-oxa-10-phosphaphenanthrene-10-oxide (compound 111)

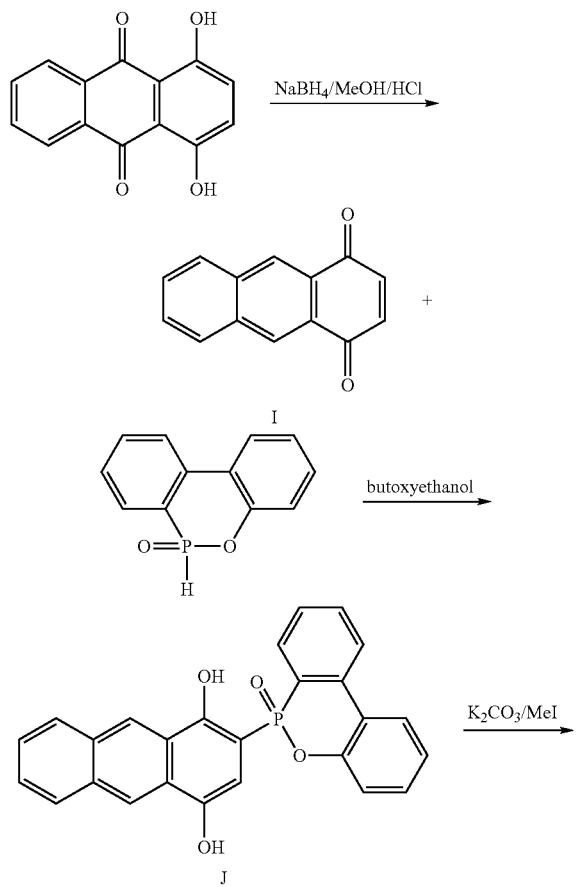

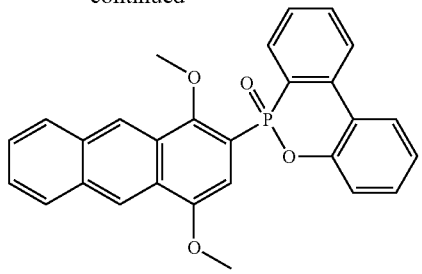

Compound 111

Synthesis of 1,4-anthraquinone (compound I)

1,4-dihydroxy-anthraquinone 25 g and methanol anhydride 250 ml are put in a 500 ml round bottom flask under argon atmosphere and NaBH$_4$ 15.7 g is slowly added at 0□. After one hour is elapsed, 6N HCL is slowly added to this mixture at 0□ to produce orange precipitates. The precipitates are filtered and then washed with water and methanol. The precipitates are reprecipitated into methylene chloride and ether to obtain targeted compound, that is, 1,4-anthraquinone (compound I) as an orange solid 15.3 g (yield: 70%).

$^1$H NMR(CDCl$_3$): δ=7.06 (d, 2H), 7.70 (q, 2H), 8.06 (q, 2H), 8.60 (s, 2H)

Synthesis of 2-(10-oxo-10H-9-oxa-10-phosphaphenanthrene-10-yl)anthracene-1,4-diol (compound J)

1.4-anthraquinone (compound I) 17 g, 9-oxa-10-phosphaphenanthrene 10-oxide 21 g, and 2-butoxyethanol 110 ml are put in a 500 ml round bottom flask under argon atmosphere. Thereafter, they are heated and recirculated for 4 hours. The 2-butoxyethanol is removed under high-temperature vacuum and is then purified with column chromatography (EA:n-Hex=1:1) to obtain targeted compound, that is, 2-(10-oxo-10H-9-oxa-10-phosphaphenanthrene-10-yl)anthracene-1,4-diol (compound J) as a solid 14.6 g (yield:42%).

$^1$H NMR (acetone-d$_6$): δ=8.46 (s, 1H), 8.25 (d, 1H), 8.20 (t, 1H), 8.04 (d, 1H), 7.89 (t, 1H), 7.84 (s, 1H), 7.78 (t, 1H), 7.64 (d, 1H), 7.55 (m, 1H), 7.49 (m, 5H), 7.29 (d, 2H), 6.73 (d, 1H)

Synthesis of 10-(1,4-dimethoxyanthracene-2-yl)-9-oxa-10-phosphaphenanthrene-10-oxide (compound 111)

2-(10-oxo-10H-9-oxa-10-phospha-phenanthrene-10-yl)-anthracene-1,4-diol 5 g, K$_2$CO$_3$ 6.5 g, CH$_3$I 5 ml, and acetone 100 ml are put in a 250 ml round flask. Thereafter, they are heated and recirculated for 4 hours. After the reaction is completed, the acetone is removed. Thereafter, this is extracted using water and ethyl acetate and then reprecipitated into THF and hexane to obtain 10-(1,4-dimethoxyanthracene-2-yl)-9-oxa-10-phosphaphenanthrene-10-oxide (compound 111) as a solid 1.5 g (yield:30%).

$^1$H NMR (acetone-d$_6$): δ=8.73 (s, 1H), 8.27 (q, 1H), 8.22 (t, 1H), 8.07 (q, 1H), 8.01 (t, 1H), 7.84 (s, 1H), 7.80 (t, 1H), 7.67 (d, 1H), 7.57 (m, 1H), 7.50 (m, 3H), 7.40 (d, 1H), 7.30 (d, 1H), 6.77 (d, 1H), 4.05 (s, 6H)

Eleventh Embodiment

Synthesis of 10-(1,4-dimethoxy-7-methyl-anthracene-2-yl)-9-oxa-10-phospha-phenanthrene 10-oxide (compound 112)

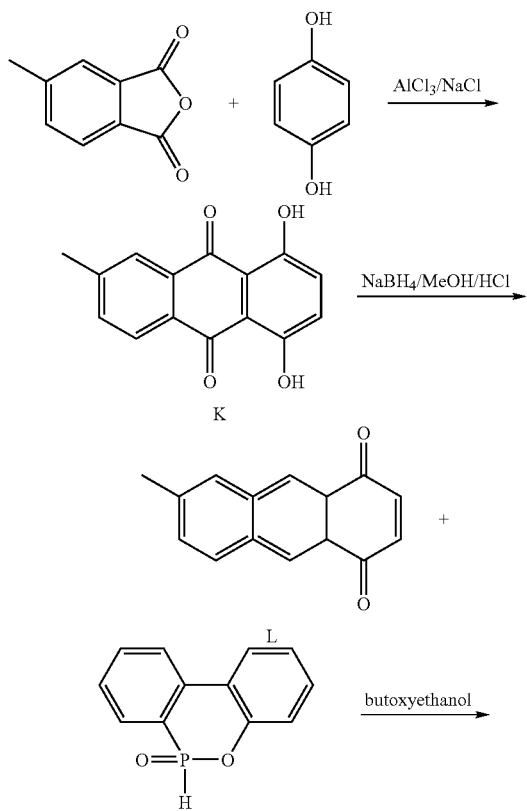

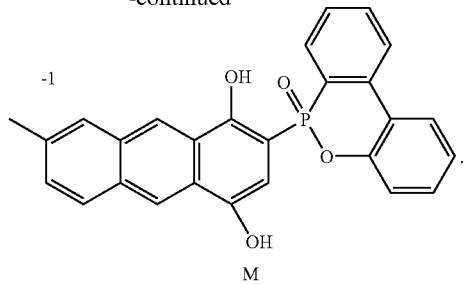

1,4-dihydroxy-6-methyl-anthraquinone (compound K)

4-methylphtal anhydride 50 g, hydroquinone 34 g, aluminum chloride 120 g, and NaCl 24 g are put in a 500 ml Erlenmeyer flask. They are is stirred at 250□ for 10 minutes. A red solid is produced during the progress of reaction. Heat is reduced and water and HCl are then added thereto to produce an orange solid. This is filtered and is then reprecipitated into THF and hexane to obtain targeted compound, that is, 1,4-dihydroxy-6-methyl-anthraquinone (compound K) as an orange solid 16.7 g (yield:35%).
$^1$H NMR(CDCl$_3$): δ=12.92 (s, 1H), 12.88 (s, 1H), 8.21 (d, 1H), 8.11 (s, 1H), 7.61 (d, 1H), 7.28 (s, 1H), 2.54 (s, 3H)

6-methyl-1,4-anthraquinone (compound L), 7-methyl-2-(10-oxo-10H-9-oxa-10-phospha-phenanthrene-10-yl)-anthracene-1,4-diol (compound M), and 10-(1,4-dimethoxy-7-methyl-anthracene-2-yl)-9-oxa-10-phospha-phenanthrene 10-oxide (compound 112) are prepared by the same method as the tenth embodiment.

Test Example

Ultraviolet and Photoluminescence Property Test

Measured values of UV-vis and photoluminescence (hereinafter, referred to as PL) for the compounds synthesized according to the present invention are listed in a table 1. Shimatzu UV/Vis spectro photometer is used for the measurement of UV-vis and LS55 luminescence spectrometer available from Perkin Elmer Co. is used for the measurement of PL. A measurement sample is prepared using dichloromethane solution. The UV-vis spectrum of the prepared sample is obtained and the PL property is obtained in a wavelength where the UV-vis peak represents a most extreme value.

TABLE 1

Compound structure and UV/PL data

| No. | Structure | Molecular formula (molecular weight) | UV(CH$_2$Cl$_2$) lmax(nm) | PL(CH$_2$Cl$_2$) lmax(nm) |
|---|---|---|---|---|
| Compound 101 | 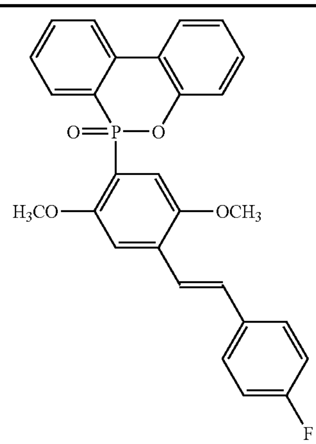 | C$_{28}$H$_{22}$FO$_4$P (472.12) | 355 | 415 |

TABLE 1-continued

Compound structure and UV/PL data

| No. | Structure | Molecular formula (molecular weight) | UV(CH$_2$Cl$_2$) lmax(nm) | PL(CH$_2$Cl$_2$) lmax(nm) |
|---|---|---|---|---|
| Compound 102 | 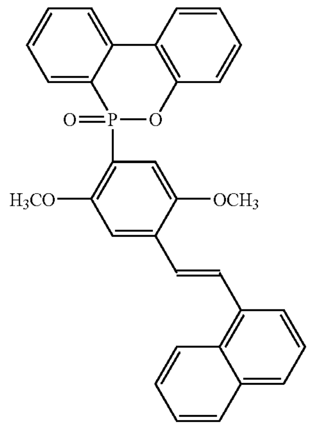 | C$_{32}$H$_{25}$O$_4$P (504.15) | 356 | 440 |
| Compound 103 | 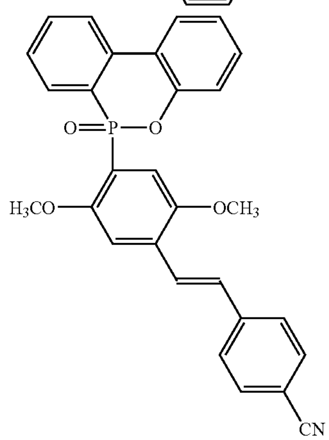 | C$_{29}$H$_{22}$NO$_4$P (479.13) | 368 | 463 |
| Compound 104 | 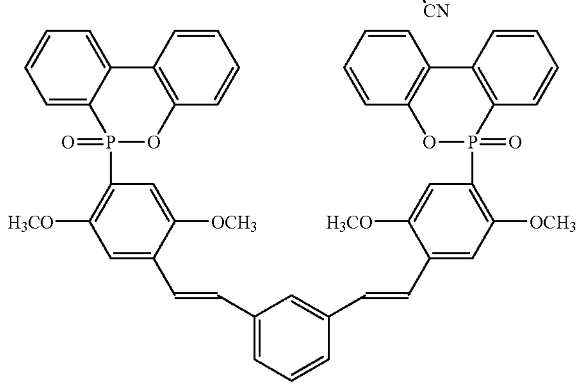 | C$_{50}$H$_{40}$O$_8$P$_2$ (830.22) | 353 | 420 |
| Compound 105 | 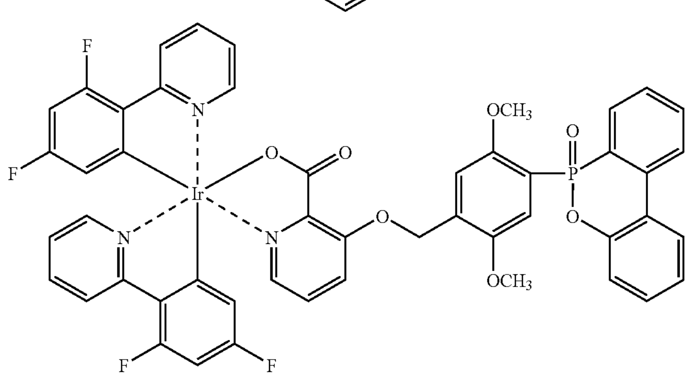 | C$_{49}$H$_{33}$F$_4$IrN$_3$O$_7$P (1075.16) | 265 | 511 |

TABLE 1-continued

Compound structure and UV/PL data

| No. | Structure | Molecular formula (molecular weight) | UV(CH$_2$Cl$_2$) lmax(nm) | PL(CH$_2$Cl$_2$) lmax(nm) |
|---|---|---|---|---|
| Compound 106 | 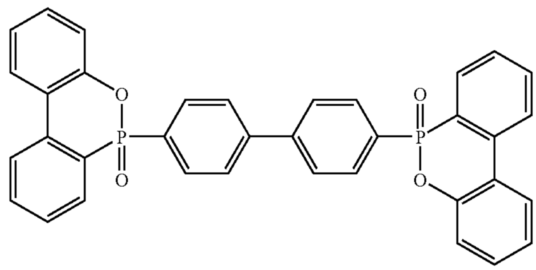 [SMILES: O=P1(c2ccc(-c3ccc(P4(=O)Oc5ccccc5-c5ccccc54)cc3)cc2)Oc2ccccc2-c2ccccc21] | C$_{36}$H$_{24}$O$_4$P$_2$ (582.11) | 270 | 407 |
| Compound 107 | 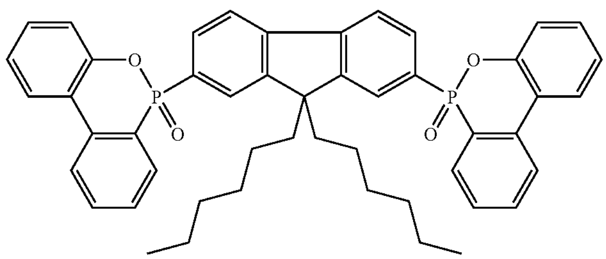 [SMILES: CCCCCCC1(CCCCCC)c2cc(P3(=O)Oc4ccccc4-c4ccccc43)ccc2-c2ccc(P3(=O)Oc4ccccc4-c4ccccc43)cc21] | C$_{49}$H$_{48}$O$_4$P$_2$ (762.30) | 318 | 345 |
| Compound 108 | 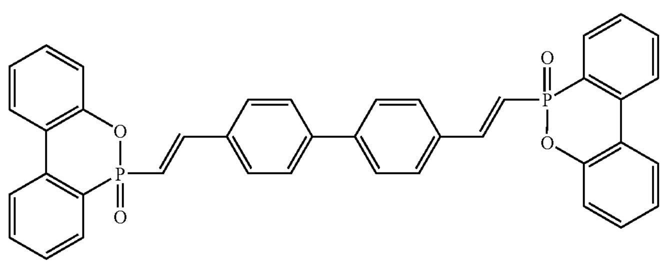 [SMILES: O=P1(/C=C/c2ccc(-c3ccc(/C=C/P4(=O)Oc5ccccc5-c5ccccc54)cc3)cc2)Oc2ccccc2-c2ccccc21] | C$_{40}$H$_{28}$O$_4$P$_2$ (634.15) | 270 | 243 |
| Compound 109 | 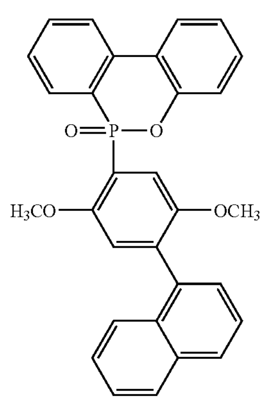 [SMILES: COc1cc(P2(=O)Oc3ccccc3-c3ccccc32)c(OC)cc1-c1cccc2ccccc12] | C$_{30}$H$_{23}$O$_4$P (478.13) | 327 | 418 |

TABLE 1-continued

Compound structure and UV/PL data

| No. | Structure | Molecular formula (molecular weight) | UV(CH$_2$Cl$_2$) lmax(nm) | PL(CH$_2$Cl$_2$) lmax(nm) |
|---|---|---|---|---|
| Compound 110 | 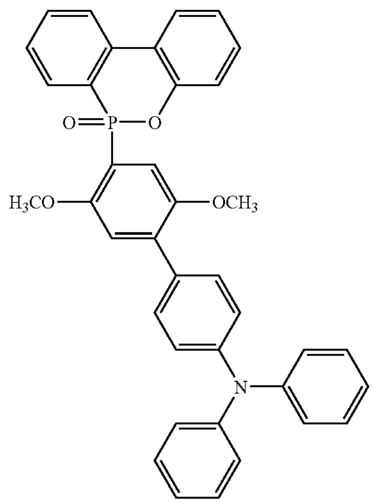 [SMILES: COc1cc(P2(=O)Oc3ccccc3-c3ccccc32)c(OC)cc1-c1ccc(N(c2ccccc2)c2ccccc2)cc1] | C$_{38}$H$_{30}$NO$_4$P (595.19) | 386 | 557 |
| Compound 111 | 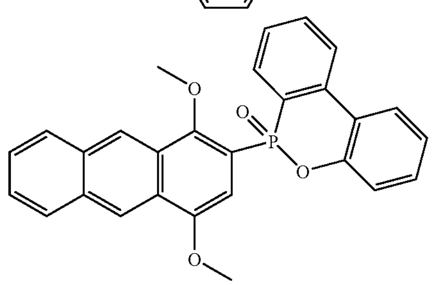 | C$_{28}$H$_{21}$O$_4$P (452.44) | 257 | 441 |
| Compound 112 | 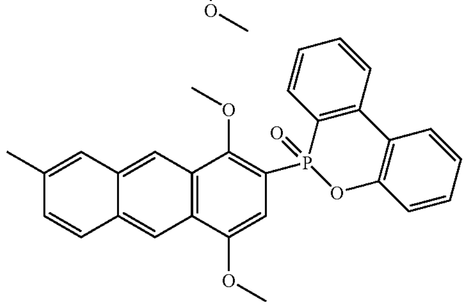 | C$_{29}$H$_{23}$O$_4$P (466.46) | 257 | 437 |

Electroluminescence Property Evaluation I

An organic light emitting diode in the most generally used form, which is configured of a cathode, a hole injecting layer, a hole transporting layer, a light emitting layer, an electron transporting layer, an electron injecting layer, and an anode, is prepared as follows in order to perform the electroluminescence (hereinafter, referred to as EL) property test.

The hole injecting layer is formed by depositing a 4,4',4"-tris(N-(2-naphthyl)-N-phenyl-amino)-triphenylamine film (hereinafter, referred to as '2-TNATA film') with a film thickness of 60 nm on a patterned ITO transparent electrode and a 4,4-bis[N-(1-naphthyl)-N-phenyl-amino]biphenyl film (hereinafter, referred to as 'NPD film') with a film thickness of 15 nm is formed on the 2-TNATA film. The NPD film functions as the hole transporting layer.

Next, the light emitting layer is formed by depositing the compound 101, the compound 103, or the compound 104 on the NPD film at a film thickness of 30 nm and a 2,9-dimethyl-4,7-diphenyl-1,10-phenanthroline film (hereinafter, referred to as 'BCP film') with a film thickness of 5 nm is deposited on the film to form a hole stopping layer. Thereafter, a tris(8-quinolinol)aluminum film (hereinafter, referred to as 'Alq film') with a film thickness of 30 nm is deposited on the film to form the electron injecting layer.

Finally, an Li/F film is formed on the film at a thickness of 1 nm and a metal Al (film thickness of 200 nm) is deposited thereon to form a metal cathode, thereby preparing the organic light emitting diode.

Electroluminescence Property Evaluation II

An organic light emitting diode in the most generally used form, which is configured of a cathode, a hole injecting layer, a hole transporting layer, a light emitting layer, an electron transporting layer, an electron injecting layer, and an anode, is prepared as follows in order to perform the electroluminescence (hereinafter, referred to as EL) property test.

The hole injecting layer is formed by depositing a 4,4',4''-tris(N-(2-naphthyl)-N-phenyl-amino)-triphenylamine film (hereinafter, referred to as '2-TNATA film') with a film thickness of 40 nm on a patterned ITO transparent electrode and a 4,4-bis[N-(1-naphthyl)-N-phenyl-amino]biphenyl film (hereinafter, referred to as 'NPD film') with a film thickness of 10 nm is formed on the 2-TNATA film. The NPD film functions as the hole transporting layer.

Next, the light emitting layer is formed by depositing the compound 112 on the NPD film at a film thickness of 40 nm and a 4,7-diphenyl-1,10-phenanthroline film (hereinafter, referred to as 'BPhen film') with a film thickness of 10 nm is deposited on the film to form a hole stopping layer.

Finally, an Li/F film is formed on the film at a thickness of 1 nm and a metal Al (film thickness of 200 nm) is deposited thereon to form a metal cathode, thereby preparing the organic light emitting diode.

The following table 2 represents the electroluminescence properties of the compound 112.

TABLE 2

| | Turn-on (V) | E.Q.E | Efficiency (cd/A) | Efficiency (lm/A) | Color coordinate (CIE) | ELmax (nm) |
|---|---|---|---|---|---|---|
| Compound 112 | 3.4 | 1.56 | 2.06 | 1.13 | 0.16, 0.16 | 450 |

INDUSTRIAL APPLICABILITY

The new phosphaphenanthrene compounds according to the present invention can be used as core materials of the OLED as well as can be used as materials for an optical switch, a sensor, a module, a wave guide, or an optical storage or amplification, non-linear optical materials, photoconductor, optical absorber, or the like.

The invention claimed is:
1. Phosphaphenanthrene compounds represented by the following Chemical Formula 1

[Chemical Formula 1]

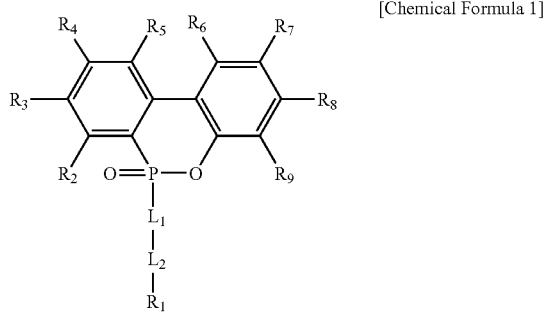

In the Chemical Formula 1,

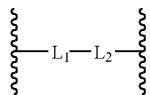

is selected from the following structures;

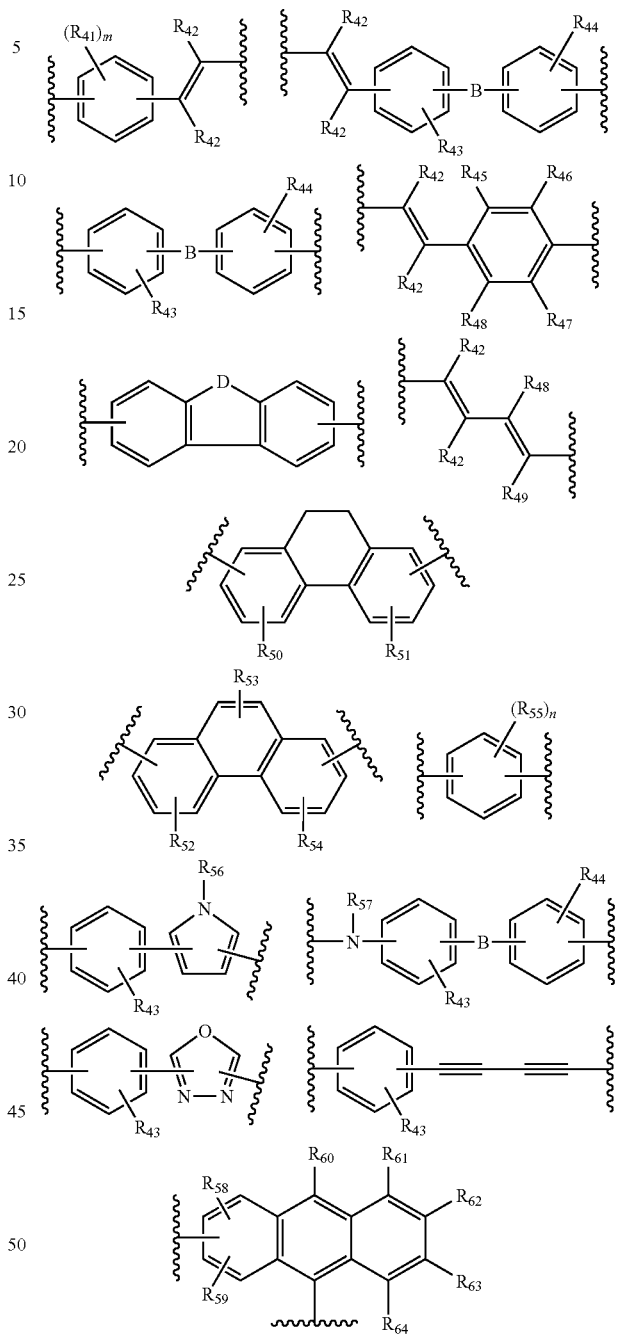

wherein

B is chemical bond or $NR_{71}$, $(O=)PR_{71}$, $SiR_{73}R_{74}$, $SO_2$, or O;

D is $CR_{81}R_{82}$, $NR_{83}$, O, S, or $SO_2$;

$R_{31}$ is $(C_1-C_{22})$ alkyl, $(C_6-C_{30})$ aryl, $(C_2-C_{10})$ alkenyl, or $(C_1-C_{22})$ alkylcarbonyl and alkyl, alkenyl, or alkycarbonyl of the $R_{31}$ may further be substituted into at least one selected from 3-member to 5-member heterocycloalkyl including at least one from N, O, and S, $(C_3-C_{22})$cycloalkyl, $(C_2-C_{10})$ alkynyl, $(C_2-C_{10})$ alkenyl, cyano, or halogen;

$R_{41}$ to $R_{64}$ are independent from each other and are hydrogen, $(C_1-C_{22})$ alkyl, $(C_6-C_{30})$ aryl, halogen, $(C_2-C_{30})$ heteroaryl, cyano, carboxylic acid, $(C_1-C_{10})$ alkylsilyl, $(C_6-C_{30})$ arylsilyl, $(C_6-C_{30})$ ar$(C_1-C_{22})$ alkyl, $(C_1-C_{22})$ alkyl$(C_6-C_{30})$aryl or $OR_{31}$, or $R_{45}$ and $R_{46}$ or $R_{47}$ and $R_{48}$ are coupled with $(C_3-C_5)$ alkylene or $(C_3-C_5)$ alkenylene to form a fused ring, and carbon of the fused ring may be substituted into heteroatoms selected from oxygen, sulfur, or nitrogen;

$R_{71}$ to $R_{74}$ are independent from each and are $(C_1-C_{22})$ alkyl, $(C_3-C_{22})$cycloalkyl, $(C_6-C_{30})$ aryl, mono- or di$(C_1-C_{10})$alkylamino, mono- or di$(C_6-C_{30})$arylamino, or amino and alkyl, cycloalkyl, or aryl of the $R_{71}$ to $R_{74}$ may further be substituted into at least one selected from halogen, $(C_1-C_{22})$ alkyl, $(C_6-C_{30})$ aryl, $(C_1-C_{22})$ alkoxy, 3-member to 7-member heterocycloalkyl including at least one of oxygen, nitrogen, or sulfur, or cyano;

$R_{81}$ to $R_{83}$ are independent from each other and are hydrogen, $(C_1-C_{22})$ alkyl, $(C_6-C_{30})$ aryl, halogen, $(C_2-C_{30})$ heteroaryl, cyano, carboxylic acid, $(C_1-C_{10})$ alkylsilyl, $(C_6-C_{30})$ arylsilyl, $(C_6-C_{30})$ar$(C_1-C_{22})$alkyl, $(C_1-C_{22})$ alkyl$(C_6-C_{30})$aryl, or $(C_1-C_{22})$alkoxy; and m and n are independent from each other and are integers of 1 to 4;

$R_1$ is hydrogen, $(C_1-C_{22})$alkyl, $(C_6-C_{30})$aryl, $(C_2-C_{30})$heteroaryl, halogen, cyano, $(C_1-C_{22})$alkoxy, $(C_6-C_{30})$aryloxy, $(C_6-C_{30})$arylsulfonyl, mono- or di$(C_1-C_{10})$alkylamino, mono- or di$(C_6-C_{30})$arylamino, $(C_2-C_7)$ alkenyloxy, $(C_2-C_7)$ alkynyloxy, $(C_2-C_7)$ alkenylcarbonyloxy, $(C_2-C_7)$ alkynylcarbonyloxy, $(C_1-C_{10})$ alkylsilyl, $(C_6-C_{30})$ arylsilyl or

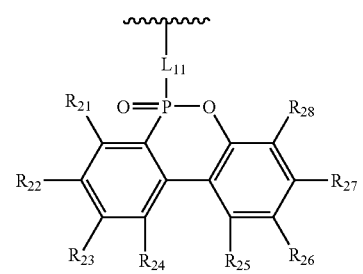

and alkyl, aryl, heteroaryl, alkoxy, aryloxy, arylsulfonyl,
  wherein alkylamino, arylamino, alkenyloxy, alkynyloxy, alkylsilyl or arylsilyl of the $R_1$ may further be substituted into at least one selected from $(C_1-C_{10})$alkyl, halogen, cyano, nitro, carboxylic acid, $(C_6-C_{30})$ aryl, mono- or di$(C_1-C_{10})$alkylamino, mono- or di$(C_6-C_{30})$arylamino, $(C_1-C_{10})$ alkylsilyl, or $(C_6-C_{30})$ arylsilyl;

$L_{11}$ is chemical bond or $(C_2-C_{10})$ alkenylene, $(C_6-C_{30})$ arylene or $NR_{16}$, and alkenylene or arylene of the $L_{11}$ may further be substituted into at least one selected from $(C_1-C_{22})$ alkyl, $(C_1-C_{22})$ alkoxy, $(C_3-C_{22})$cycloalkyl, $(C_6-C_{30})$ aryl, cyano, halogen, amino, mono- or di$(C_1-C_{10})$alkylamino, mono- or di$(C_6-C_{30})$arylamino, nitro, or hydroxy;

$R_2$ to $R_9$ are independent from each other and are hydrogen, $(C_1-C_{22})$ alkyl, $(C_1-C_{22})$ alkyl including oxygen, nitrogen, or sulfur, $(C_1-C_{22})$ alkoxy, $(C_3-C_{22})$ cycloalkyl, $(C_3-C_{22})$cycloalkyl $(C_1-C_{22})$ alkyl, $(C_6-C_{30})$ aryl, halogen, cyano, amino, mono- or di$(C_1-C_{10})$alkylamino, mono- or di$(C_6-C_{30})$arylamino, hydroxy, nitro, mono- or di-benzylamino, or $(C_3-C_{10})$cycloalkylamino and the $R_2$ to $R_9$ are combined with carbon of neighboring substitutent by $(C_3-C_5)$ alkylene or $(C_3-C_5)$ alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_2$ to $R_9$ may further be substituted into at least one selected from $(C_1-C_{10})$ alkyl, halogen, $(C_6-C_{30})$ aryl, $(C_1-C_{10})$ alkylsilyl, or $(C_6-C_{30})$ arylsilyl;

$R_{16}$ is $(C_1-C_{22})$ alkyl, $(C_3-C_{22})$cycloalkyl, $(C_6-C_{30})$ aryl, mono- or di$(C_1-C_{10})$alkylamino, mono- or di$(C_6-C_{30})$ arylamino, or amino, and alkyl, cycloalkyl, or aryl of the $R_{11}$ to $R_{16}$ may further be substituted into at least one selected from halogen, $(C_1-C_{22})$ alkyl, $(C_6-C_{30})$ aryl, $(C_1-C_{22})$ alkoxy, 3-member to 7-member heterocycloalkyl including at least one of oxygen, nitrogen, or sulfur, or cyano; and $R_{21}$ to $R_{28}$ are independent from each other and are hydrogen, $(C_1-C_{22})$ alkyl, $(C_1-C_{22})$ alkyl including oxygen, nitrogen, or sulfur, $(C_1-C_{22})$ alkoxy, $(C_3-C_{22})$cycloalkyl, $(C_3-C_{22})$cycloalkyl $(C_1-C_{22})$alkyl, $(C_6-C_{30})$aryl, halogen, cyano, amino, mono- or di$(C_1-C_{10})$alkylamino, mono- or di$(C_6-C_{30})$arylamino, hydroxy, nitro, mono- or di-benzylamino, or $(C_3-C_{10})$cycloalkylamino and the $R_{21}$ to $R_{28}$ are combined with carbon of neighboring substitutent by $(C_3-C_5)$ alkylene or $(C_3-C_5)$ alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_{21}$ to $R_{28}$ may further be substituted into at least one selected from $(C_1-C_{10})$ alkyl, halogen, $(C_6-C_{30})$ aryl, $(C_1-C_{10})$ alkylsilyl, or $(C_6-C_{30})$ arylsilyl.

2. Phosphaphenanthrene compounds represented by the following chemical formula 1

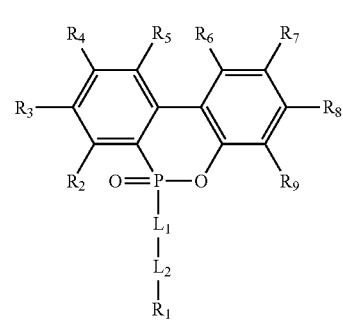

[Chemical Formula 1]

In the Chemical Formula 1,

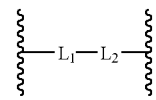

is selected from the following structures;

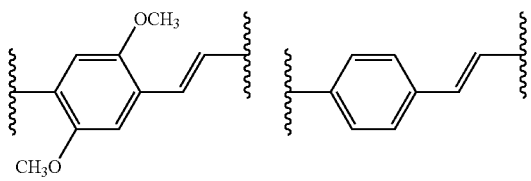

-continued
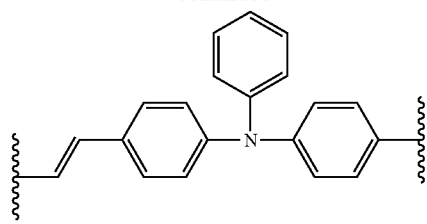
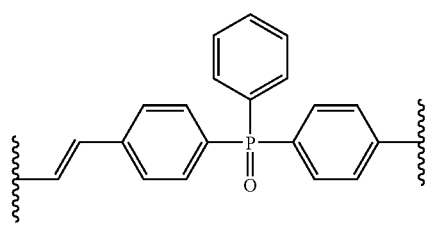
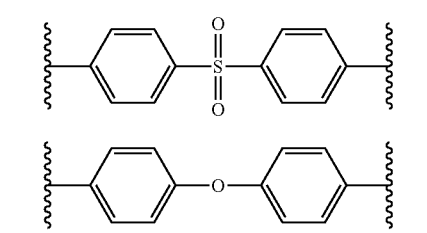
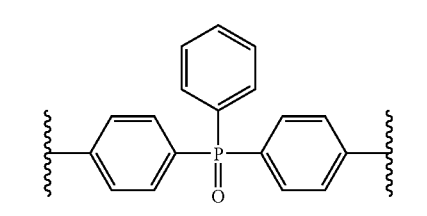
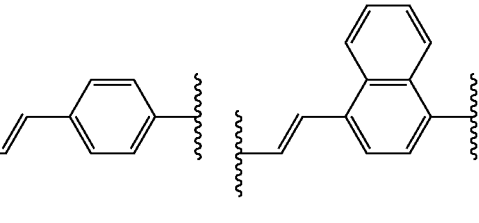
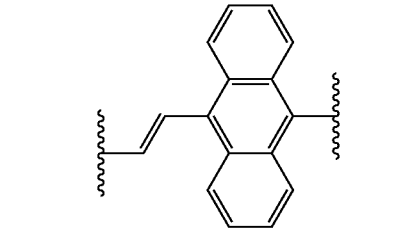
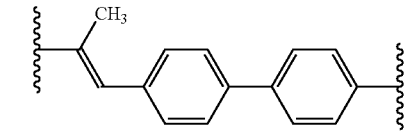
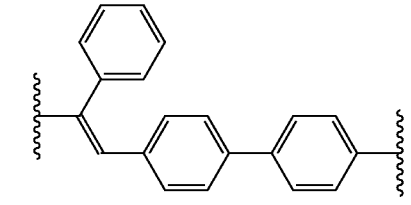
-continued
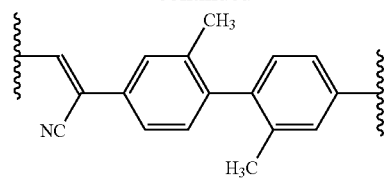
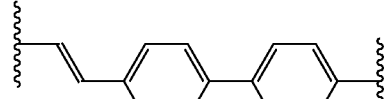
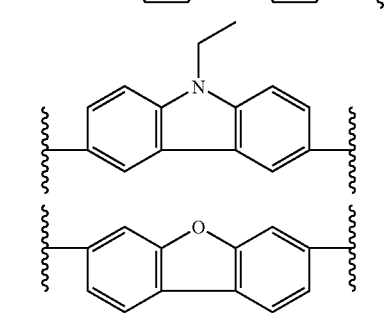
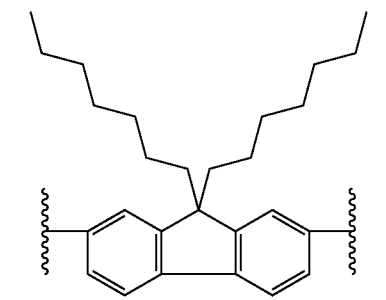
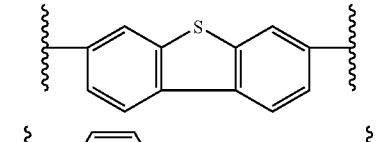
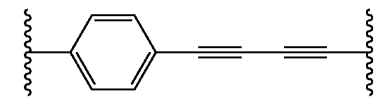
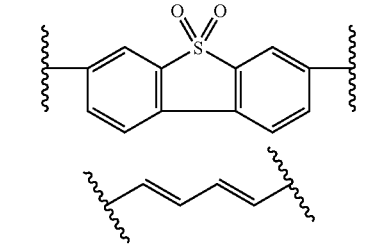
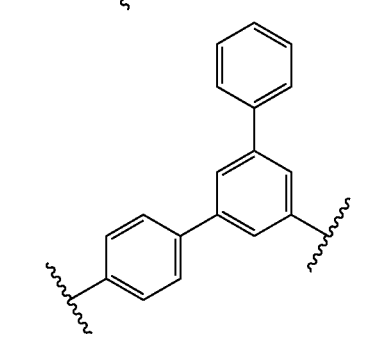

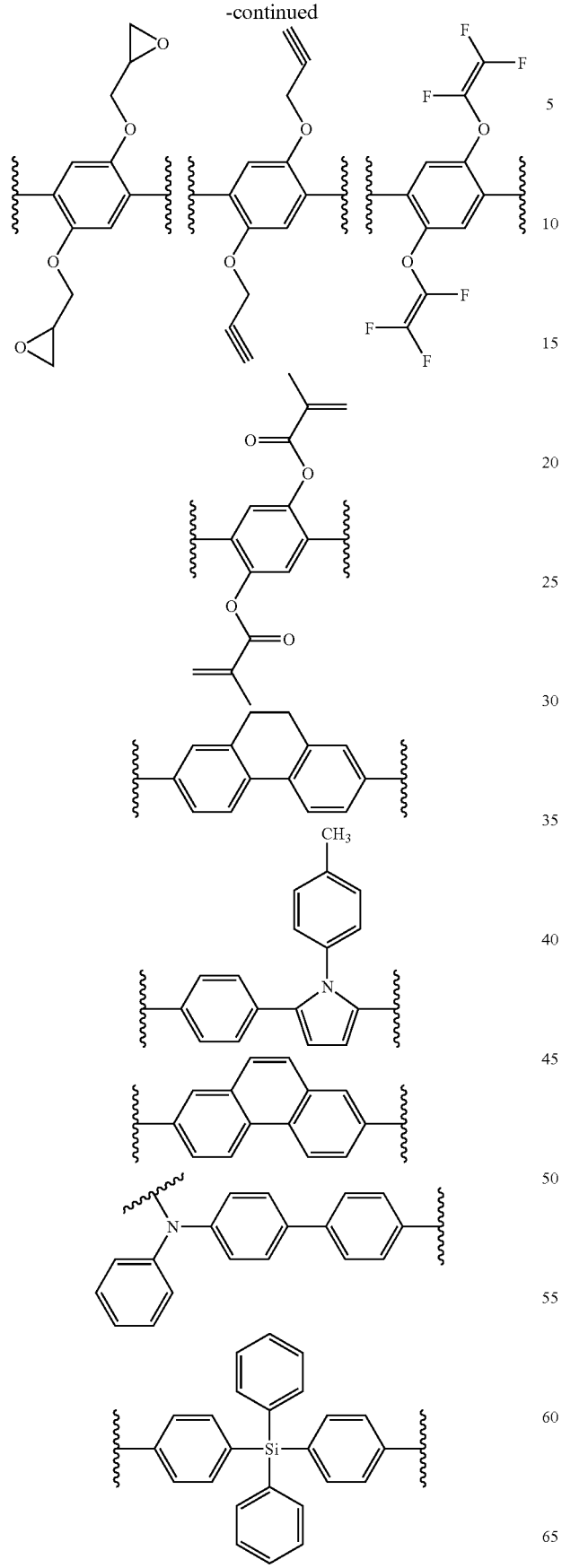
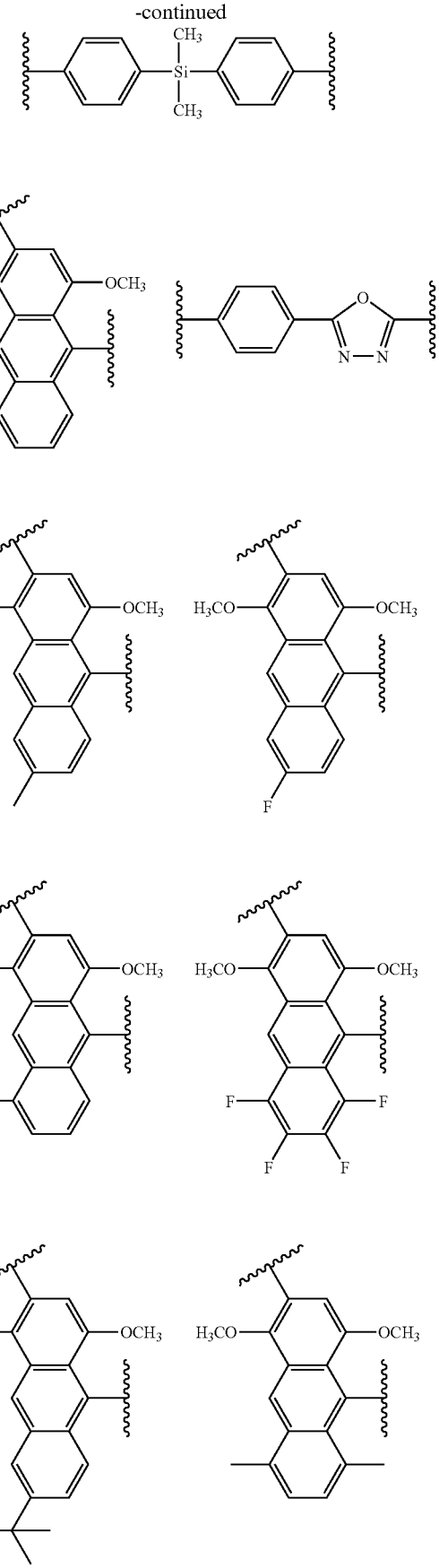

-continued

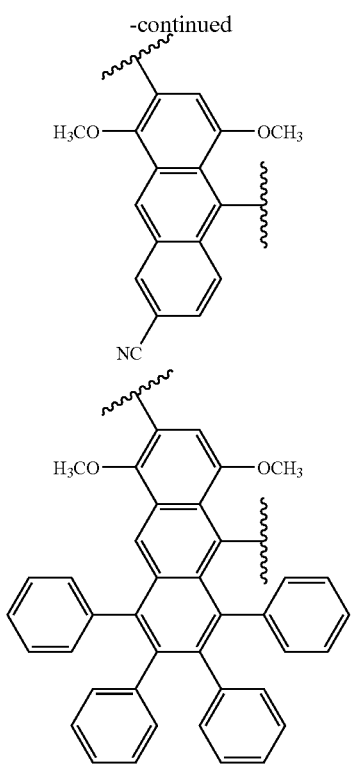

wherein
$R_1$ is hydrogen, $(C_1\text{-}C_{22})$alkyl, $(C_6\text{-}C_{30})$ aryl, $(C_2\text{-}C_{30})$ heteroaryl, halogen, cyano, $(C_1\text{-}C_{22})$alkoxy, $(C_6\text{-}C_{30})$ aryloxy, $(C_6\text{-}C_{30})$ arylsulfonyl, mono- or di$(C_1\text{-}C_{10})$alkylamino, mono- or di$(C_6\text{-}C_{30})$arylamino, $(C_2\text{-}C_7)$ alkenyloxy, $(C_2\text{-}C_7)$ alkynyloxy, $(C_2\text{-}C_7)$ alkenylcarbonyloxy, $(C_2\text{-}C_7)$ alkynylcarbonyloxy, $(C_1\text{-}C_{10})$ alkylsilyl, $(C_6\text{-}C_{30})$ arylsilyl or

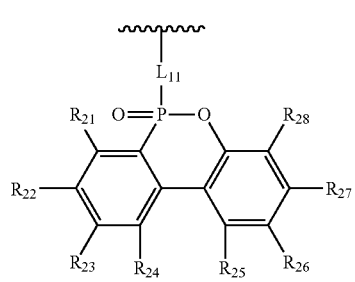

and alkyl, aryl, heteroaryl, alkoxy, aryloxy, arylsulfonyl,
wherein alkylamino, arylamino, alkenyloxy, alkynyloxy, alkylsilyl or arylsilyl of the $R_1$ may further be substituted into at least one selected from $(C_1\text{-}C_{10})$alkyl, halogen, cyano, nitro, carboxylic acid, $(C_6\text{-}C_{30})$ aryl, mono- or di$(C_1\text{-}C_{10})$alkylamino, mono- or di$(C_6\text{-}C_{30})$arylamino, $(C_1\text{-}C_{10})$ alkylsilyl, or $(C_6\text{-}C_{30})$ arylsilyl;
$L_{11}$ is chemical bond or $(C_2\text{-}C_{10})$ alkenylene, $(C_6\text{-}C_{30})$ arylene or $NR_{16}$, and alkenylene or arylene of the $L_{11}$ may further be substituted into at least one selected from $(C_1\text{-}C_{22})$ alkyl, $(C_1\text{-}C_{22})$ alkoxy, $(C_3\text{-}C_{22})$cycloalkyl, $(C_6\text{-}C_{30})$ aryl, cyano, halogen, amino, mono- or di$(C_1\text{-}C_{10})$alkylamino, mono- or di$(C_6\text{-}C_{30})$arylamino, nitro, or hydroxy;

$R_2$ to $R_9$ are independent from each other and are hydrogen, $(C_1\text{-}C_{22})$ alkyl, $(C_1\text{-}C_{22})$ alkyl including oxygen, nitrogen, or sulfur, $(C_1\text{-}C_{22})$alkoxy, $(C_3\text{-}C_{22})$cycloalkyl, $(C_3\text{-}C_{22})$cycloalkyl $(C_1\text{-}C_{22})$ alkyl, $(C_6\text{-}C_{30})$ aryl, halogen, cyano, amino, mono- or di$(C_1\text{-}C_{10})$alkylamino, mono- or di$(C_6\text{-}C_{30})$arylamino, hydroxy, nitro, mono- or di-benzylamino, or $(C_3\text{-}C_{10})$cycloalkylamino and the $R_2$ to $R_9$ are combined with carbon of neighboring substitutent by $(C_3\text{-}C_5)$ alkylene or $(C_3\text{-}C_5)$ alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_2$ to $R_9$ may further be substituted into at least one selected from $(C_1\text{-}C_{10})$ alkyl, halogen, $(C_6\text{-}C_{30})$ aryl, $(C_1\text{-}C_{10})$ alkylsilyl, or $(C_6\text{-}C_{30})$ arylsilyl;

$R_{16}$ is $(C_1\text{-}C_{22})$ alkyl, $(C_3\text{-}C_{22})$cycloalkyl, $(C_6\text{-}C_{30})$ aryl, mono- or di$(C_1\text{-}C_{10})$alkylamino, mono- or di$(C_6\text{-}C_{30})$ arylamino, or amino, and alkyl, cycloalkyl, or aryl of the $R_{11}$ to $R_{16}$ may further be substituted into at least one selected from halogen, $(C_1\text{-}C_{22})$ alkyl, $(C_6\text{-}C_{30})$ aryl, $(C_1\text{-}C_{22})$ alkoxy, 3-member to 7-member heterocycloalkyl including at least one of oxygen, nitrogen, or sulfur, or cyano; and $R_{21}$ to $R_{28}$ are independent from each other and are hydrogen, $(C_1\text{-}C_{22})$ alkyl, $(C_1\text{-}C_{22})$ alkyl including oxygen, nitrogen, or sulfur, $(C_1\text{-}C_{22})$alkoxy, $(C_3\text{-}C_{22})$cycloalkyl, $(C_3\text{-}C_{22})$cycloalkyl $(C_1\text{-}C_{22})$ alkyl, $(C_6\text{-}C_{30})$ aryl, halogen, cyano, amino, mono- or di$(C_1\text{-}C_{10})$alkylamino, mono- or di$(C_6\text{-}C_{30})$arylamino, hydroxy, nitro, mono- or di-benzylamino, or $(C_3\text{-}C_{10})$cycloalkylamino and the $R_{21}$ to $R_{28}$ are combined with carbon of neighboring substitutent by $(C_3\text{-}C_5)$ alkylene or $(C_3\text{-}C_5)$ alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_{21}$ to $R_{28}$ may further be substituted into at least one selected from $(C_1\text{-}C_{10})$ alkyl, halogen, $(C_6\text{-}C_{30})$ aryl, $(C_1\text{-}C_{10})$ alkylsilyl, or $(C_6\text{-}C_{30})$ arylsilyl.

3. The phosphaphenanthrene compounds according to claim 2, wherein it is selected from the following compounds;

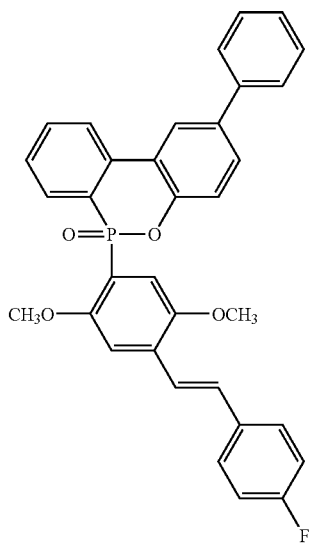

61
-continued
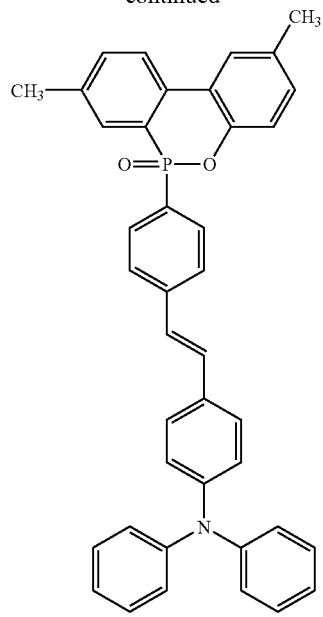
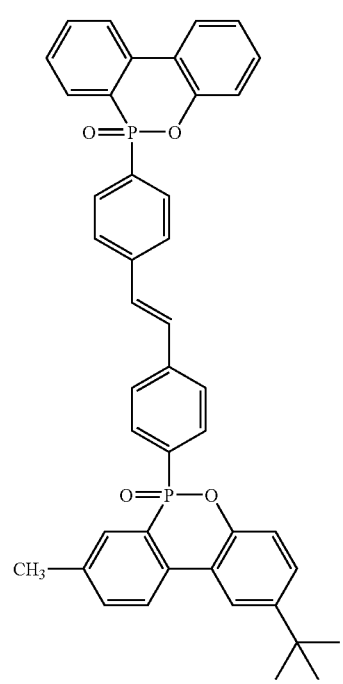
62
-continued
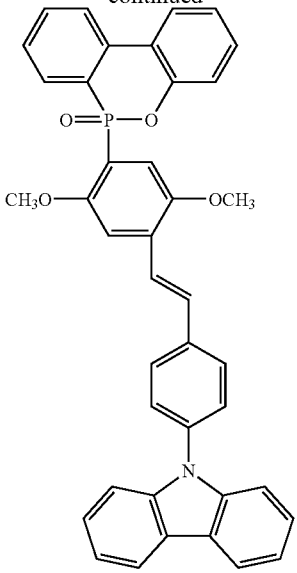
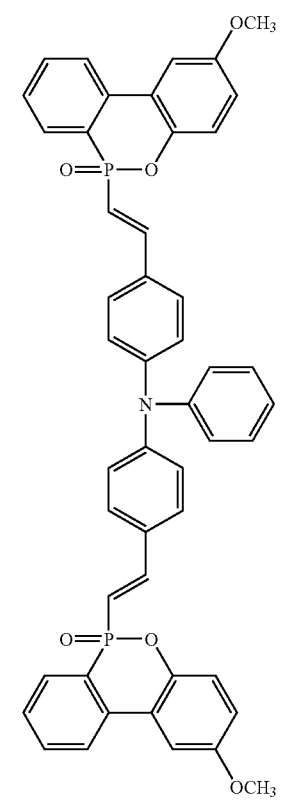

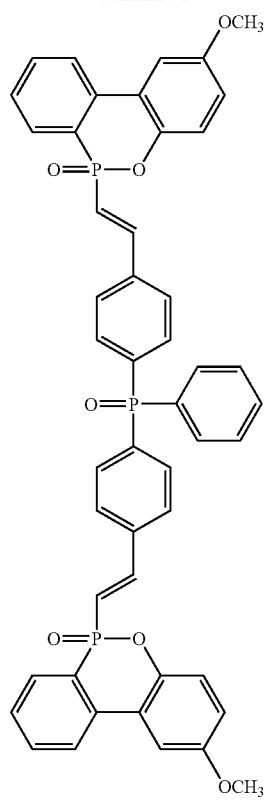
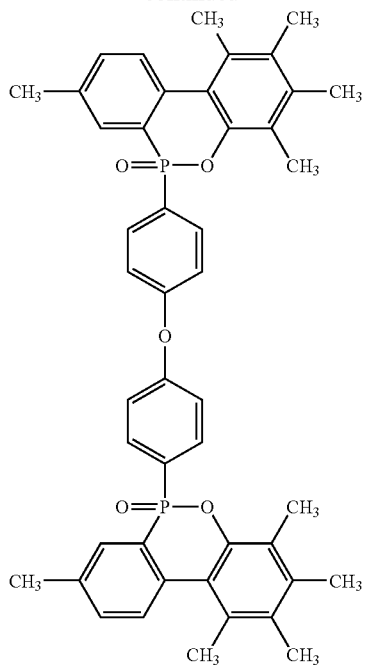
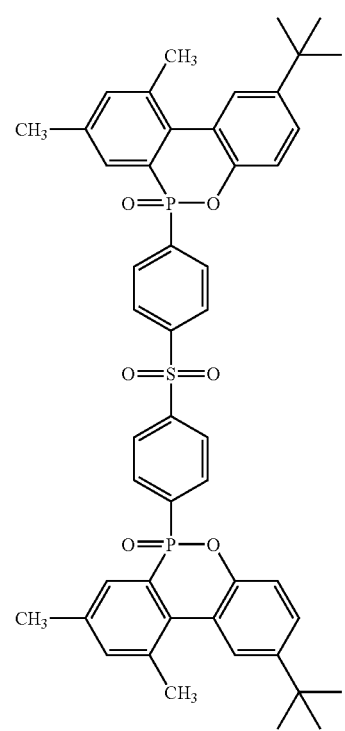
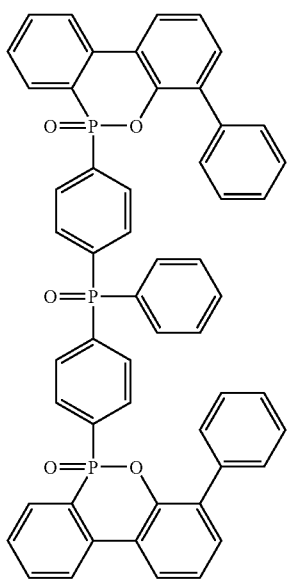

65
-continued
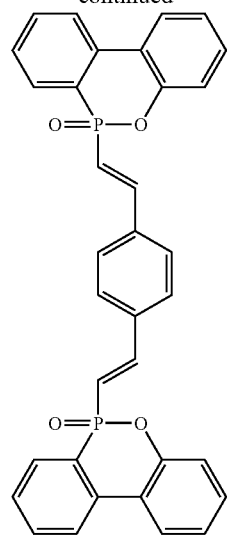
66
-continued
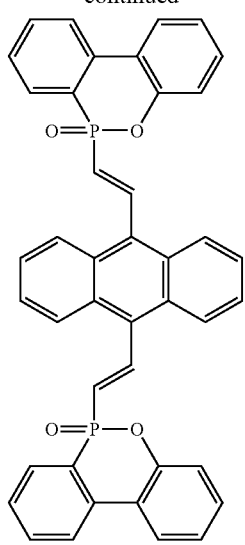
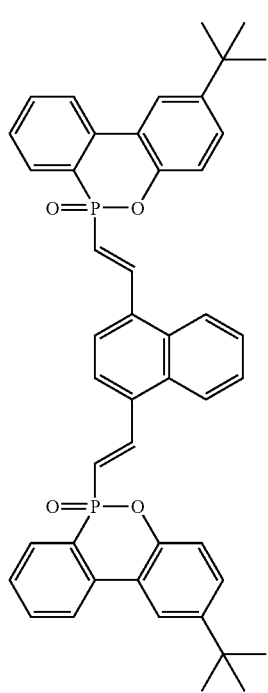
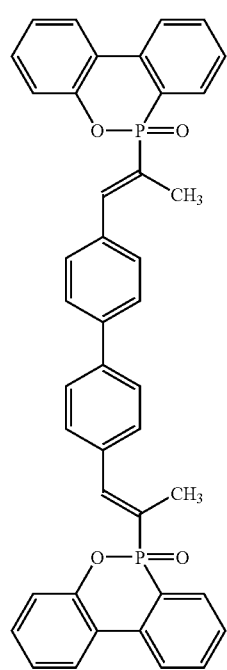

67
-continued
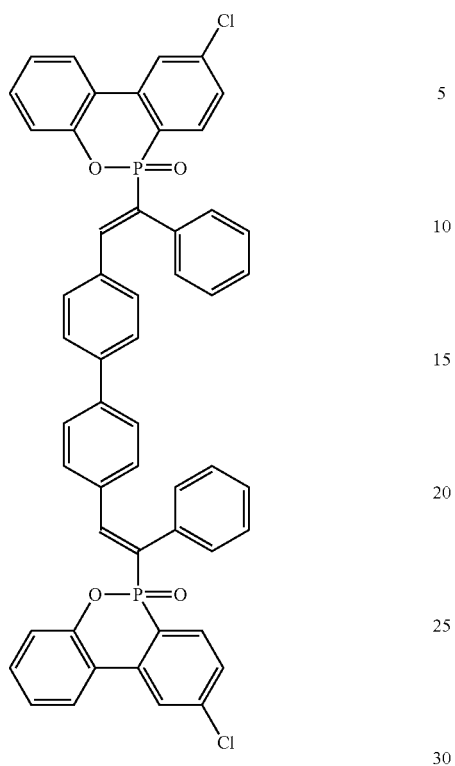
68
-continued
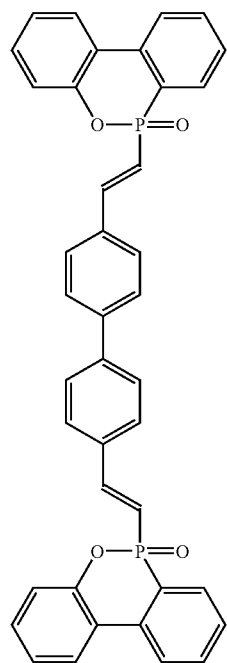
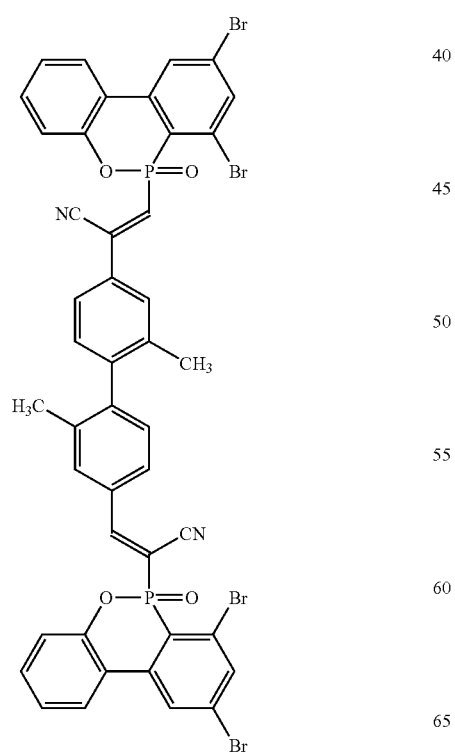
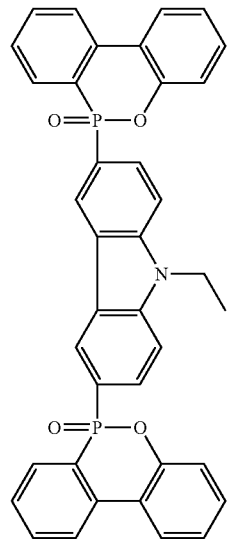

69
-continued
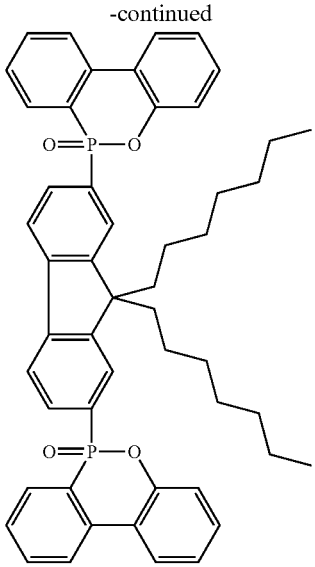
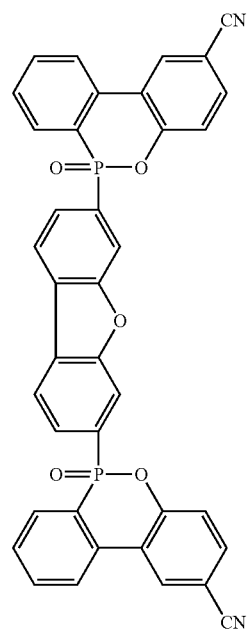
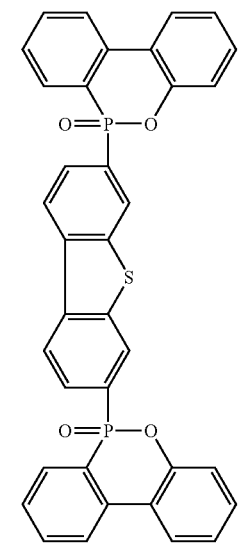
70
-continued
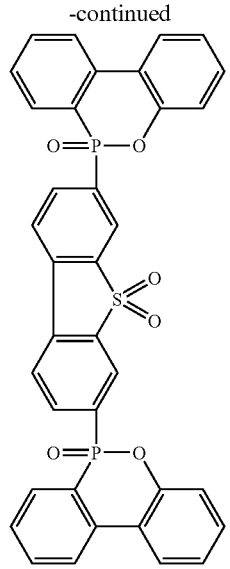
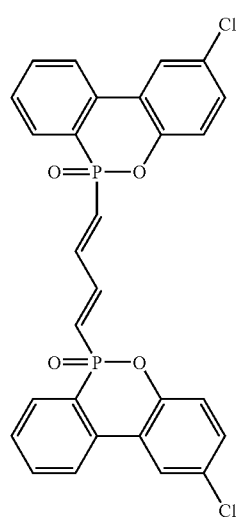
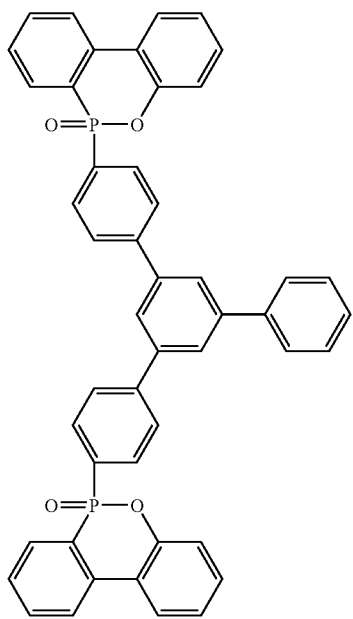

71
-continued
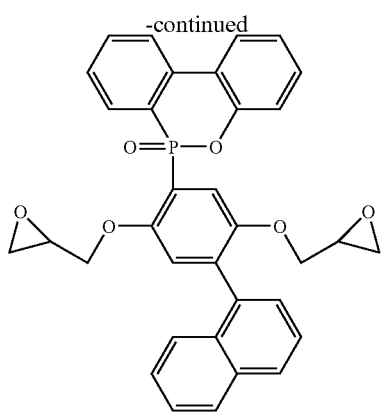
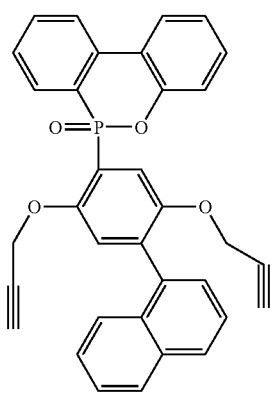
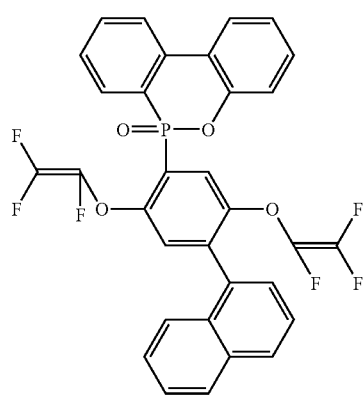
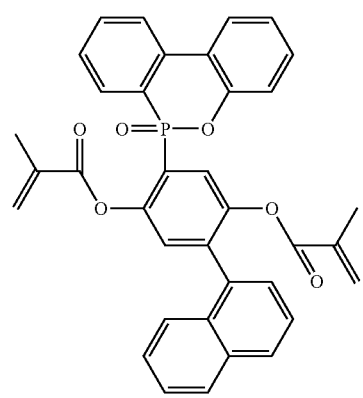
72
-continued
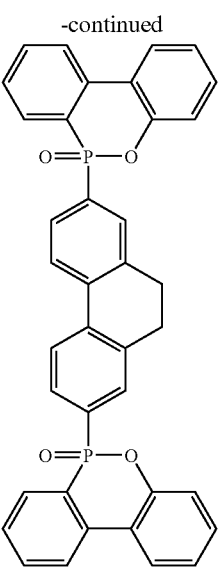
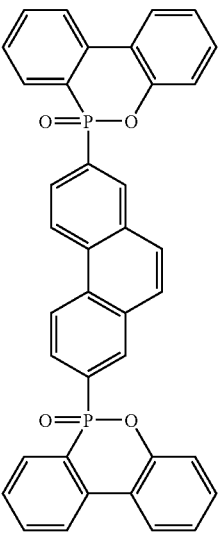

-continued
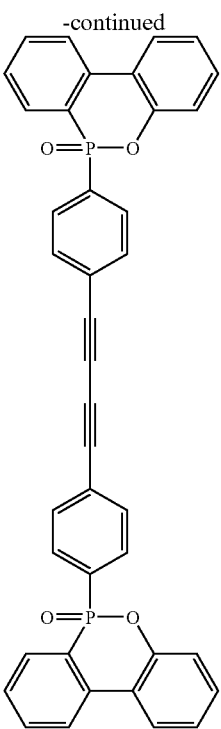
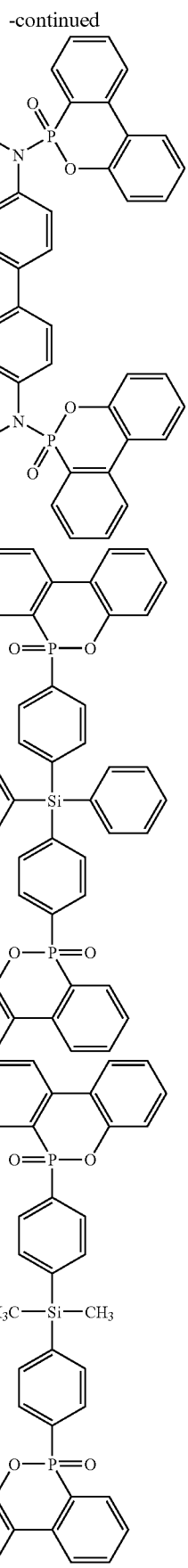

75
-continued
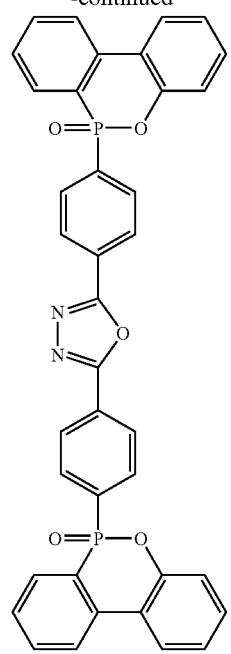
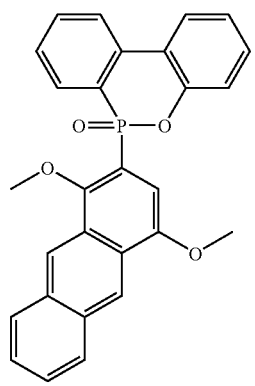
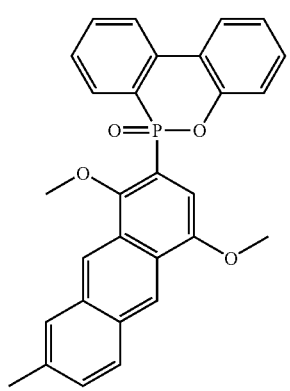
76
-continued
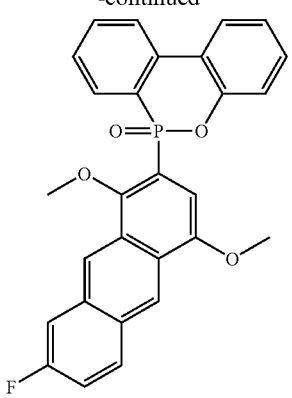
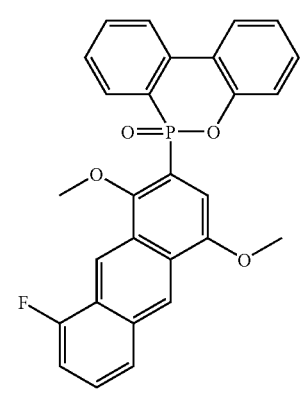
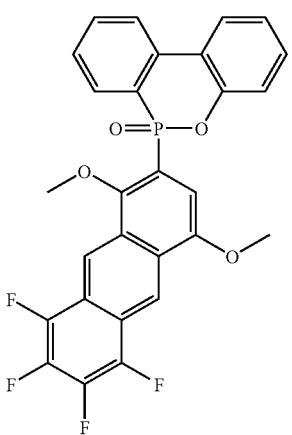

-continued

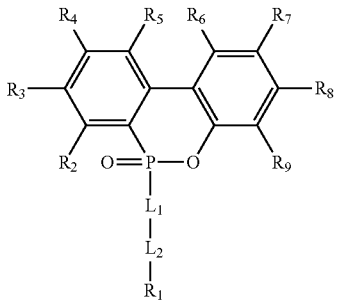

4. An organic light emitting diode including phosphaphenanthrene compounds represented by the following chemical formula 1

[Chemical Formula 1]

In the chemical formula 1, $L_1$ is chemical bond or $(C_2\text{-}C_{10})$ alkenylene, $(C_6\text{-}C_{30})$ arylene or $NR_{11}$, and alkenylene or arylene of the $L_1$ may further be substituted into at least one selected from $(C_1\text{-}C_{22})$ alkyl, $(C_6\text{-}C_{30})$ aryl, $(C_2\text{-}C_{30})$ heteroaryl, $(C_6\text{-}C_{30})$ ar $(C_1\text{-}C_{22})$alkyl, $(C_1\text{-}C_{22})$alkyl$(C_6\text{-}C_{30})$aryl, halogen, $(C_1\text{-}C_{10})$ alkylsilyl, $(C_6\text{-}C_{30})$arylsilyl, carboxylic acid, cyano, or $OR_{31}$;

$L_2$ is $(C_2\text{-}C_{10})$ alkenylene, $(C_2\text{-}C_{10})$ alkynylene, $(C_6\text{-}C_{30})$ arylene, $(C_2\text{-}C_{30})$ heteroarylene or —$Ar_1$-$A$-$Ar_2$—, and alkenylene, arylene, or heteroarylene of the $L_2$ may further be substituted into at least one selected from $(C_1\text{-}C_{22})$ alkyl, halogen, cyano, carboxylic acid, $(C_1\text{-}C_{10})$ alkylsilyl, $(C_6\text{-}C_{30})$ arylsilyl, $(C_6\text{-}C_{30})$ aryl, $(C_2\text{-}C_{30})$ heteroaryl, $(C_6\text{-}C_{30})$ar $(C_1\text{-}C_{22})$alkyl, $(C_1\text{-}C_{22})$alkyl $(C_6\text{-}C_{30})$aryl or $OR_{31}$;

$Ar_1$ and $Ar_2$ are independent from each other and are $(C_6\text{-}C_{30})$ arylene or $(C_2\text{-}C_{30})$ heteroarylene, Arylene or heteroarylene of the $Ar_1$ and $Ar_2$ may further be substituted into at least one selected from $(C_1\text{-}C_{22})$alkyl, $(C_6\text{-}C_{30})$ aryl, $(C_6\text{-}C_{30})$ aryloxy, $(C_2\text{-}C_{30})$heteroaryl, halogen, $(C_1\text{-}C_{10})$ alkylsilyl, $(C_6\text{-}C_{30})$ arylsilyl, $(C_1\text{-}C_{22})$alkoxy, carboxylic acid or cyano;

A is $NR_{12}$, $(O=)PR_{13}$, $SiR_{14}R_{15}$, $SO_2$ or 0;

$R_1$ is hydrogen, $(C_1\text{-}C_{22})$alkyl, $(C_6\text{-}C_{30})$aryl, $(C_2\text{-}C_{30})$heteroaryl, halogen, cyano, $(C_1\text{-}C_{22})$alkoxy, $(C_6\text{-}C_{30})$ aryloxy, $(C_6\text{-}C_{30})$ arylsulfonyl, mono- or di$(C_1\text{-}C_{10})$alkylamino, mono- or di$(C_6\text{-}C_{30})$arylamino, $(C_2\text{-}C_7)$ alkenyloxy, $(C_2\text{-}C_7)$ alkynyloxy, $(C_2\text{-}C_7)$ alkenylcarbonyloxy, $(C_2\text{-}C_7)$ alkynylcarbonyloxy, $(C_1\text{-}C_{10})$ alkylsilyl, $(C_6\text{-}C_{30})$ arylsilyl or and alkyl, aryl, heteroaryl, alkoxy, aryloxy, arylsulfonyl, wherein alkylamino, arylamino, alkenyloxy, alkynyloxy, alkylsilyl or arylsilyl of the $R_1$ may further be substituted into at least one selected from $(C_1-C_{10})$alkyl, halogen, cyano, nitro, carboxylic acid, $(C_6-C_{30})$ aryl, mono- or di$(C_1-C_{10})$alkylamino, mono- or di$(C_6-C_{30})$arylamino, $(C_1-C_{10})$ alkylsilyl, or $(C_6-C_{30})$ arylsilyl;

$L_{11}$ is chemical bond or $(C_2-C_{10})$ alkenylene, $(C_6-C_{30})$ arylene or $NR_{16}$, and alkenylene or arylene of the $L_{11}$ may further be substituted into at least one selected from $(C_1-C_{22})$ alkyl, $(C_1-C_{22})$ alkoxy, $(C_3-C_{22})$cycloalkyl, $(C_6-C_{30})$ aryl, cyano, halogen, amino, mono- or di$(C_1-C_{10})$alkylamino, mono- or di$(C_6-C_{30})$arylamino, nitro, or hydroxy;

$R_2$ to $R_9$ are independent from each other and are hydrogen, $(C_1-C_{22})$ alkyl, $(C_1-C_{22})$ alkyl including oxygen, nitrogen, or sulfur, $(C_1-C_{22})$alkoxy, $(C_3-C_{22})$cycloalkyl, $(C_3-C_{22})$cycloalkyl $(C_1-C_{22})$ alkyl, $(C_6-C_{30})$ aryl, halogen, cyano, amino, mono- or di$(C_1-C_{10})$alkylamino, mono- or di$(C_6-C_{30})$arylamino, hydroxy, nitro, mono- or di-benzylamino, or $(C_3-C_{10})$cycloalkylamino and the $R_2$ to $R_9$ are combined with carbon of neighboring substitutent by $(C_3-C_5)$ alkylene or $(C_3-C_5)$ alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_2$ to $R_9$ may further be substituted into at least one selected from $(C_1-C_{10})$ alkyl, halogen, $(C_6-C_{30})$ aryl, $(C_1-C_{10})$ alkylsilyl, or $(C_6-C_{30})$ arylsilyl;

$R_{11}$ to $R_{16}$ are independent from each other and are $(C_1-C_{22})$ alkyl, $(C_3-C_{22})$cycloalkyl, $(C_6-C_{30})$ aryl, mono- or di$(C_1-C_{10})$alkylamino, mono- or di$(C_6-C_{30})$arylamino, or amino, and alkyl, cycloalkyl, or aryl of the $R_{11}$ to $R_{16}$ may further be substituted into at least one selected from halogen, $(C_1-C_{22})$ alkyl, $(C_6-C_{30})$ aryl, $(C_1-C_{22})$ alkoxy, 3-member to 7-member heterocycloalkyl including at least one of oxygen, nitrogen, or sulfur, or cyano;

$R_{21}$ to $R_{28}$ are independent from each other and are hydrogen, $(C_1-C_{22})$ alkyl, $(C_1-C_{22})$ alkyl including oxygen, nitrogen, or sulfur, $(C_1-C_{22})$alkoxy, $(C_3-C_{22})$cycloalkyl, $(C_3-C_{22})$cycloalkyl $(C_1-C_{22})$ alkyl, $(C_6-C_{30})$ aryl, halogen, cyano, amino, mono- or di$(C_1-C_{10})$alkylamino, mono- or di$(C_6-C_{30})$arylamino, hydroxy, nitro, mono- or di-benzylamino, or $(C_3-C_{10})$cycloalkylamino and the $R_{21}$ to $R_{28}$ are combined with carbon of neighboring substitutent by $(C_3-C_5)$ alkylene or $(C_3-C_5)$ alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_{21}$ to $R_{28}$ may further be substituted into at least one selected from $(C_1-C_{10})$alkyl, halogen, $(C_6-C_{30})$ aryl, $(C_1-C_{10})$ alkylsilyl, or $(C_6-C_{30})$ arylsilyl; and $R_{31}$ is $(C_1-C_{22})$ alkyl, $(C_6-C_{30})$ aryl, $(C_2-C_{10})$ alkenyl, or $(C_1-C_{22})$ alkylcarbonyl and alkyl, aryl, or alkycarbonyl of the $R_{31}$ may further be substituted into at least one selected from 3-member to 5-member heterocycloalkyl including at least one from N, O, and S, $(C_3-C_{22})$cycloalkyl, $(C_2-C_{10})$ alkynyl, $(C_2-C_{10})$alkenyl, cyano, or halogen.

5. The organic light emitting diode according to claim 4, wherein the phosphaphenanthrene compounds are included in a layer selected from an electron transporting layer, a light emitting layer, or a mixing function layer thereof.

6. An organic semiconductor device including the phosphaphenanthrene compounds represented by the following Chemical Formula 1

[Chemical Formula 1]

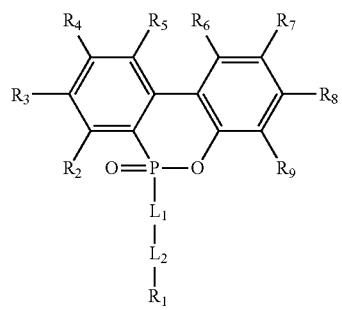

in the chemical formula 1, $L_1$ is chemical bond or $(C_2-C_{10})$ alkenylene, $(C_6-C_{30})$ arylene or $NR_{11}$, and alkenylene or arylene of the $L_1$ may further be substituted into at least one selected from $(C_1-C_{22})$ alkyl, $(C_6-C_{30})$ aryl, $(C_2-C_{30})$ heteroaryl, $(C_6-C_{30})$ ar $(C_1-C_{22})$alkyl, $(C_1-C_{22})$alkyl$(C_6-C_{30})$aryl, halogen, $(C_1-C_{10})$ alkylsilyl, $(C_6-C_{30})$arylsilyl, carboxylic acid, cyano, or $OR_{31}$;

$L_2$ is $(C_2-C_{10})$ alkenylene, $(C_2-C_{10})$ alkynylene, $(C_6-C_{30})$ arylene, $(C_2-C_{30})$ heteroarylene or —$Ar_1$-A-$Ar_2$—, and alkenylene, arylene, or heteroarylene of the $L_2$ may further be substituted into at least one selected from $(C_1-C_{22})$ alkyl, halogen, cyano, carboxylic acid, $(C_1-C_{10})$ alkylsilyl, $(C_6-C_{30})$ arylsilyl, $(C_6-C_{30})$ aryl, $(C_2-C_{30})$ heteroaryl, $(C_6-C_{30})$ar $(C_1-C_{22})$alkyl, $(C_1-C_{22})$ alkyl $(C_6-C_{30})$ aryl or $OR_{31}$;

$Ar_1$ and $Ar_2$ are independent from each other and are $(C_6-C_{30})$ arylene or $(C_2-C_{30})$ heteroarylene, Arylene or heteroarylene of the $Ar_1$ and $Ar_2$ may further be substituted into at least one selected from $(C_1-C_{22})$alkyl, $(C_6-C_{30})$ aryl, $(C_6-C_{30})$ aryloxy, $(C_2-C_{30})$heteroaryl, halogen, $(C_1-C_{10})$ alkylsilyl, $(C_6-C_{30})$ arylsilyl, $(C_1-C_{22})$alkoxy, carboxylic acid or cyano;

A is $NR_{12}$, (O=)$PR_{13}$, $SiR_{14}R_{15}$, $SO_2$ or O;

$R_1$ is hydrogen, $(C_1-C_{22})$alkyl, $(C_6-C_{30})$aryl, $(C_2-C_{30})$heteroaryl, halogen, cyano, $(C_1-C_{22})$alkoxy, $(C_6-C_{30})$ aryloxy, $(C_6-C_{30})$ arylsulfonyl, mono- or di$(C_1-C_{10})$alkylamino, mono- or di$(C_6-C_{30})$arylamino, $(C_2-C_7)$ alkenyloxy, $(C_2-C_7)$ alkynyloxy, $(C_2-C_7)$ alkenylcarbonyloxy, $(C_2-C_7)$ alkynylcarbonyloxy, $(C_1-C_{10})$ alkylsilyl, $(C_6-C_{30})$ arylsilyl or

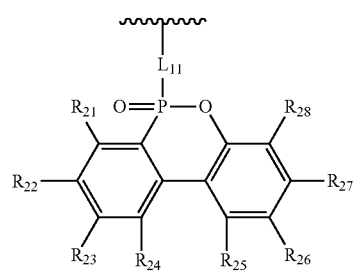

and alkyl, aryl, heteroaryl, alkoxy, aryloxy, arylsulfonyl, wherein alkylamino, arylamino, alkenyloxy, alkynyloxy, alkylsilyl or arylsilyl of the $R_1$ may further be substituted into at least one selected from $(C_1-C_{10})$alkyl, halogen, cyano, nitro, carboxylic acid, $(C_6-C_{30})$ aryl, mono- or di($C_1$-$C_{10}$)alkylamino, mono- or di($C_6$-$C_{30}$)arylamino, ($C_1$-$C_{10}$) alkylsilyl, or ($C_6$-$C_{30}$) arylsilyl;

$L_{11}$ is chemical bond or ($C_2$-$C_{10}$) alkenylene, ($C_6$-$C_{30}$) arylene or $NR_{16}$, and alkenylene or arylene of the $L_{11}$ may further be substituted into at least one selected from ($C_1$-$C_{22}$) alkyl, ($C_1$-$C_{22}$) alkoxy, ($C_3$-$C_{22}$)cycloalkyl, ($C_6$-$C_{30}$) aryl, cyano, halogen, amino, mono- or di($C_1$-$C_{10}$)alkylamino, mono- or di($C_6$-$C_{30}$)arylamino, nitro, or hydroxy;

$R_2$ to $R_9$ are independent from each other and are hydrogen, ($C_1$-$C_{22}$) alkyl, ($C_1$-$C_{22}$) alkyl including oxygen, nitrogen, or sulfur, ($C_1$-$C_{22}$)alkoxy, ($C_3$-$C_{22}$)cycloalkyl, ($C_3$-$C_{22}$)cycloalkyl ($C_1$-$C_{22}$) alkyl, ($C_6$-$C_{30}$) aryl, halogen, cyano, amino, mono- or di($C_1$-$C_{10}$)alkylamino, mono- or di($C_6$-$C_{30}$)arylamino, hydroxy, nitro, mono- or di-benzylamino, or ($C_3$-$C_{10}$)cycloalkylamino and the $R_2$ to $R_9$ are combined with carbon of neighboring substitutent by ($C_3$-$C_5$) alkylene or ($C_3$-$C_5$) alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_2$ to $R_9$ may further be substituted into at least one selected from ($C_1$-$C_{10}$) alkyl, halogen, ($C_6$-$C_{30}$) aryl, ($C_1$-$C_{10}$) alkylsilyl, or ($C_6$-$C_{30}$) arylsilyl;

$R_{11}$ to $R_{16}$ are independent from each other and are ($C_1$-$C_{22}$) alkyl, ($C_3$-$C_{22}$)cycloalkyl, ($C_6$-$C_{30}$) aryl, mono- or di($C_1$-$C_{10}$)alkylamino, mono- or di($C_6$-$C_{30}$)arylamino, or amino, and alkyl, cycloalkyl, or aryl of the $R_{11}$ to $R_{16}$ may further be substituted into at least one selected from halogen, ($C_1$-$C_{22}$) alkyl, ($C_6$-$C_{30}$) aryl, ($C_1$-$C_{22}$) alkoxy, 3-member to 7-member heterocycloalkyl including at least one of oxygen, nitrogen, or sulfur, or cyano;

$R_{21}$ to $R_{28}$ are independent from each other and are hydrogen, ($C_1$-$C_{22}$) alkyl, ($C_1$-$C_{22}$) alkyl including oxygen, nitrogen, or sulfur, ($C_1$-$C_{22}$)alkoxy, ($C_3$-$C_{22}$)cycloalkyl, ($C_3$-$C_{22}$)cycloalkyl ($C_1$-$C_{22}$) alkyl, ($C_6$-$C_{30}$) aryl, halogen, cyano, amino, mono- or di($C_1$-$C_{10}$)alkylamino, mono- or di($C_6$-$C_{30}$)arylamino, hydroxy, nitro, mono- or di-benzylamino, or ($C_3$-$C_{10}$)cycloalkylamino and the $R_{21}$ to $R_{28}$ are combined with carbon of neighboring substitutent by ($C_3$-$C_5$) alkylene or ($C_3$-$C_5$) alkenylene to form a fused ring, carbon of the fused ring may be substituted into heteroatoms selected from oxygen, sulfur, or nitrogen, alkyl, alkoxy, cycloalkyl, cycloalkylalkyl, aryl, or amino of the $R_{21}$ to $R_{28}$ may further be substituted into at least one selected from ($C_1$-$C_{10}$) alkyl, halogen, ($C_6$-$C_{30}$) aryl, ($C_1$-$C_{10}$) alkylsilyl, or ($C_6$-$C_{30}$) arylsilyl; and $R_{31}$ is ($C_1$-$C_{22}$) alkyl, ($C_6$-$C_{30}$) aryl, ($C_2$-$C_{10}$) alkenyl, or ($C_1$-$C_{22}$) alkylcarbonyl and alkyl, aryl, or alkycarbonyl of the $R_{31}$ may further be substituted into at least one selected from 3-member to 5-member heterocycloalkyl including at least one from N, O, and S, ($C_3$-$C_{22}$)cycloalkyl, ($C_2$-$C_{10}$) alkynyl, ($C_2$-$C_{10}$) alkenyl, cyano, or halogen.

7. An organic light emitting diode including the phosphaphenanthrene compounds according to claim 1.

8. An organic light emitting diode including the phosphaphenanthrene compounds according to claim 2.

9. An organic light emitting diode including the phosphaphenanthrene compounds according to claim 3.

10. The organic light emitting diode according to claim 7, wherein the phosphaphenanthrene compounds are included in a layer selected from an electron transporting layer, a light emitting layer, or a mixing function layer thereof.

11. The organic light emitting diode according to claim 8, wherein the phosphaphenanthrene compounds are included in a layer selected from an electron transporting layer, a light emitting layer, or a mixing function layer thereof.

12. The organic light emitting diode according to claim 9, wherein the phosphaphenanthrene compounds are included in a layer selected from an electron transporting layer, a light emitting layer, or a mixing function layer thereof.

13. An organic semiconductor device including the phosphaphenanthrene compounds according to claim 1.

14. An organic semiconductor device including the phosphaphenanthrene compounds according to claim 2.

15. An organic semiconductor device including the phosphaphenanthrene compounds according to claim 3.

* * * * *